US012808862B2

(12) United States Patent
Debad et al.

(10) Patent No.: US 12,808,862 B2
(45) Date of Patent: Nov. 24, 2026

(54) GENETIC MARKER AND/OR BIOMARKERS FOR TRAUMATIC BRAIN INJURY, AND ULTRASENSITIVE ASSAYS FOR BIOMARKERS OF TRAUMATIC BRAIN INJURY

(71) Applicant: Meso Scale Technologies, LLC., Rockville, MD (US)

(72) Inventors: Jeff Debad, Gaithersburg, MD (US); Arianna Biesso, Columbia, MD (US)

(73) Assignee: Meso Scale Technologies, LLC., Rockville, MD (US)

( * ) Notice: Subject to any disclaimer, the term of this patent is extended or adjusted under 35 U.S.C. 154(b) by 0 days.

(21) Appl. No.: 18/666,008

(22) Filed: May 16, 2024

(65) Prior Publication Data

US 2024/0302359 A1 Sep. 12, 2024

Related U.S. Application Data

(62) Division of application No. 16/978,464, filed as application No. PCT/US2019/021333 on Mar. 8, 2019.

(60) Provisional application No. 62/640,220, filed on Mar. 8, 2018, provisional application No. 62/666,328, filed on May 3, 2018, provisional application No. 62/672,263, filed on May 16, 2018.

(51) Int. Cl.
*G01N 33/53* (2006.01)
*G01N 21/66* (2006.01)
*G01N 35/02* (2006.01)

(52) U.S. Cl.
CPC ......... *G01N 33/5308* (2013.01); *G01N 21/66* (2013.01); *G01N 35/02* (2013.01); *G01N 2201/0484* (2013.01); *G01N 2800/28* (2013.01)

(58) Field of Classification Search
CPC .... G01N 33/5308; G01N 21/66; G01N 35/02; G01N 2201/0484; G01N 2800/28; G01N 2333/4709; G01N 33/6896
See application file for complete search history.

(56) References Cited

U.S. PATENT DOCUMENTS 4,168,146 A 9/1979 Grubb et al.
4,235,601 A 11/1980 Stallmo et al.
4,366,241 A 12/1982 Tom et al.
4,442,204 A 4/1984 Greenquist et al.
5,208,535 A 5/1993 Nakayama et al.
5,807,522 A 9/1998 Brown et al.
6,110,426 A 8/2000 Shalon et al.
6,977,772 B2 12/2005 Yoshida
12,339,275 B2 * 6/2025 Debad ................ G01N 33/6896
2003/0113713 A1 6/2003 Glezer et al.
2003/0207290 A1 11/2003 Kenten et al.
2004/0022677 A1 2/2004 Wohlstadter et al.
2004/0189311 A1 9/2004 Glezer et al.
2005/0052646 A1 3/2005 Wohlstadter et al.
2005/0142033 A1 6/2005 Glezer et al.
2006/0205012 A1 9/2006 Debad et al.
2011/0201099 A1 8/2011 Anderson et al.
2014/0272939 A1 9/2014 Aghvanyan et al.
2015/0140127 A1 5/2015 Ramirez et al.
2021/0048431 A1 2/2021 Debad et al.

FOREIGN PATENT DOCUMENTS

WO 99/26067 A1 5/1999
WO 2004/058055 A2 7/2004
WO 2004/059293 A2 7/2004
WO 2011/032155 A2 3/2011
WO 2014/165061 A1 10/2014
WO 2015/175856 A1 11/2015
WO 2016/055148 A2 4/2016

OTHER PUBLICATIONS

Whisstock et al. Quaterly Reviews of Biophysics, 2003, "Prediction of protein function from protein sequence and structure", 36(3): 307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10: 8-9. (Year: 2002).*
Castranio E.L. et al., "Gene Co-Expression Networks Identify Trem2 and Tyrobp as Major Hubs in Human APOE Expressing Mice Following Traumatic Brain Injury", Neurobiology of Disease 105:1-14 (2017).
Dibattista A.P. et al., "Blood Biomarkers in Moderate-to-Severe Traumatic Brain Injury: Potential Utility of a Multi- Marker Approach in Characterizing Outcome", Frontiers in Neurology 6(110):1-9 (May 2015).
Jordan B.D. et al., "Apolipoprotein E ϵ4 Associated With Chronic Traumatic Brain Injury in Boxing", JAMA 278 (2):136-140 (Jul. 9, 1997).
Neselius S. et al., "Increased CSF Levels of Phosphorylated Neurofilament Heavy Protein Following Bout in Amateur Boxers", PLoS One 8(11):e81249 (Nov. 2013).
Nikolenko G.N. et al., "Accurate Measurement of Tau in Serum and Plasma Using a Novel Technology With fg/ mL Sensitivity", retrieved from the Internet: URL:https://www.mesoscale.com/-/media/files/scientific%20poster/ctad_2015_human_taus-plex_immunoassay.pdf [retrieved on Apr. 16, 2019] (Jan. 2015).
Rezeli M. et al., "Quantification of Total Apolipoprotein E and its Specific Isoforms in Cerebrospinal Fluid and Blood in Alzheimer's Disease and Other Neurodegenerative Diseases", EuPA Open Proteomics 8:137-143 (2015).

(Continued)

*Primary Examiner* — Iqbal H Chowdhury
(74) *Attorney, Agent, or Firm* — Scully, Scott, Murphy & Presser, P.C.

(57) ABSTRACT

The present invention relates to assays, methods, and kits to assess traumatic brain injury (TBI) in a subject. The present invention also relates to ultrasensitive assays for GFAP, tau, CKBB, IL-1β, IL-2, IL-6, IL-10, IL-22, IP-10, TNFα, TSLP, NFL, and/or NFH.

13 Claims, 5 Drawing Sheets

(56) References Cited

OTHER PUBLICATIONS

Suschak J.M. et al., "True Sensitivity of Immunoassays: Are Concentrations of Low Abundance Analytes Real or Artifacts?", J. Immunol., vol. 196, Supplement 1, retrieved from the Internet: URL:https://www.mesoscale.com/-/media/files/scientific%20poster/sensitivity-s-plex-immunoassays-low-abundance-analytes-aai-2016.pdf [retrieved on Apr. 16, 2019] (May 1, 2016).

Anonymous, "R-PLEX Antibody Set, Human GFAP", Meso Scale Diagnostics, L.L.C., (Sep. 2017), retrieved from the Internet: URL:https://www.mesoscale.com/-/media/files/data%20sheets/r-plex%20human%20gfap.pdf [retrieved on Apr. 12, 2019].

Anonymous, "R-PLEX Antibody Set, Human ApoE", Meso Scale Diagnostics, L.L.C., (Jan. 2018), retrieved from the Internet: URL:https://www.mesoscale.com/-/media/files/data%20sheets/ds-r-plex-human-apoe.pdf [retrieved on Apr. 12, 2019].

International Search Report dated May 3, 2019 received in International Application No. PCT/US2019/021333.

Canadian Examination Report dated Jan. 2, 2024 received in Canadian Application No. 3,093,455.

European Examination Report dated Jul. 19, 2023 received in European Application No. 19 712 465.4.

Khetani S. et al., "Polyethylenimine Modified Graphene-Oxide Electrochemical Immunosensor for the Detection of Glial Fibrillary Acidic Protein in Central Nervous System Injury", ACS Sensors 3(4):844-851 (Mar. 8, 2018).

Oberoi P. et al., "True Sensitivity of Immunoassays: Are Concentrations of Low Abundance Analytes Real or Artifacts", J. Immunol. 196(1):138.9 (May 1, 2016), Abstract.

Canadian Examination Report dated Sep. 12, 2024 received in Canadian Application No. 3,093,455.

European Extended Search Report dated Oct. 28, 2024 received in European Application No. 24 18 0409.5.

Extended European Search Report dated Nov. 24, 2025 received in European Application No. 25 19 8930.7.

European Communication dated Apr. 10, 2026 received in European Application No. 24 180 409.5.

European Communication dated May 12, 2026 received in European Application No. 19 712 465.4.

* cited by examiner

A

B

Ultrasensitive Assay

GENETIC MARKER AND/OR BIOMARKERS FOR TRAUMATIC BRAIN INJURY, AND ULTRASENSITIVE ASSAYS FOR BIOMARKERS OF TRAUMATIC BRAIN INJURY

CROSS REFERENCE TO RELATED APPLICATIONS

The present application is a divisional of co-pending application Ser. No. 16/978,464, filed Sep. 4, 2020, which is a National Stage Entry of International Application No. PCT/US2019/021333, filed Mar. 8, 2019, which claims priority of U.S. Provisional Application Nos. 62/672,263, filed May 16, 2018; 62/666,328, filed May 3, 2018 and 62/640,220, filed Mar. 8, 2018, the entire contents of which are incorporated herein by reference.

STATEMENT REGARDING FEDERALLY-SPONSORED RESEARCH

This invention was made with federal support under R01NS067417 from the National Institute for Neurological Disorders and Stroke (NINDS), U24AI118663 from the National Institutes of Health, a Research Supplement to Promote Diversity in Health-Related Research R01NS067417-S1, T32NS041218 from Georgetown University's Neural Injury and Plasticity Training Program supported by the NINDS, and W911NF-12-R-001 and W81XWH-13-C-0196, both awarded by the Department of Defense. The U.S. government has certain rights in the invention.

FIELD OF THE INVENTION

This application relates to assays, modules, kits, and methods useful in assessing traumatic brain injury (TBI). It also relates to ultrasensitive assays for biomarkers of TBI.

BACKGROUND OF THE INVENTION

A need exists for more accurate methods, for example, diagnosing, prognosing, and monitoring recovery from, of assessing traumatic brain injury (TBI). Medical and other experts have recently recognized the important impact of TBI in, for example, sports and the military. This is true for moderate TBI, severe TBI, and single or multiple episodes of mild TBI (mTBI). In addition, experts believe that multiple episodes of mTBI lead to acute and chronic adverse sequelae. Such sequelae could be avoided if mTBI were detected or diagnosed more accurately.

Although biomarkers and other objective criteria are known for assessing severe TBI, such criteria are not yet known for mTBI. Likewise, factors that predispose subjects to the debilitating, chronic effects of mTBI are not yet known. In addition, potentially confounding effects of genetics on the accurate detection and measurement of biomarkers in moderate or severe TBI have not been determined.

A need also exists for measuring the very low levels of GFAP and other biomarkers in samples such that assessing TBI in patients is improved.

SUMMARY OF THE INVENTION

The present invention provides an assay and methods to detect or measure biomarkers to more accurately assess TBI, including mild, moderate and severe TBI. It further provides an assay and methods to monitor or prevent sequelae of TBI and other related methods. The methods of the present invention can be used to triage and guide the treatment of individuals who have experienced TBI, including multiple episodes of mTBI.

The present invention also provides ultrasensitive assays for GFAP and other biomarkers of TBI. This aspect can be combined with or independent of the other TBI aspects, such as APOE4+ status, of the present application.

The present inventors have carried out clinical and animal studies that led to several important findings. First, although the APOE4 (apolipoprotein E) allele is protective of the acute effects of mTBI, it is not protective of the sequelae of mTBI. Second, the protective effects of APOE4 apparently leads to over-representation of APOE4-carrying people (heterozygous and homozygous) in occupations in which they are prone to experience repeated mTBI, and are therefore susceptible to mTBI sequela. Third, although it was known blood glial fibrillary acidic protein (GFAP) increases in TBI (0.5 ng/ml), GFAP was not detected in mild TBI or in normal subjects. Thus, the inventors developed an ultrasensitive assay that is able, for the first time, to detect GFAP levels in normal subjects, and subsequently discovered that GFAP levels also increase in mTBI. GFAP is therefore useful in diagnosing all forms of TBI. Fourth, however, the inventors discovered that GFAP does not increase in APOE4-carrying people with mTBI. Thus, the inventors concluded that, in the absence of a test for APOE4, APOE4-carrying mTBI subjects would be misdiagnosed as not having mTBI.

Similarly, the GFAP levels in APOE4 subjects with moderate or severe TBI would be lower than the levels in subjects who do not carry this allele. Thus, the inventors concluded that methods, such as diagnosis, prognosis, and monitoring of recovery, that rely on GFAP levels would be inaccurate in such APOE4 subjects in the absence of testing for the APOE4 allele.

One gene that has been long-associated with outcome after severe TBI is the APOE gene. Following severe TBI, the APOE4 allele is associated with worse outcomes including longer coma times,[1] poor long-term prognosis[2] and an increased risk of developing Alzheimer's disease compared to non-APOE4 carriers.[3, 4] The APOE4 allele is also associated with more severe chronic traumatic encephalopathy (CTE) symptoms in boxers,[5] and a mixed pathology of both amyloid and tau in the CTE brain.[6] In preclinical studies on stroke and trauma, APOE4 mice have increased amyloid and tau pathology and experience worse outcomes compared to APOE3 mice.[7-9] However, APOE4 has not been studied in mTBI, and the relationship between GFAP levels with APOE4 has not previously been studied.

In the current study, the inventors hypothesized that if the APOE4 allele was responsible for acute adverse events following mTBI, then this allele should be underrepresented in a professional boxing cohort. The inventors further hypothesized that plasma levels of GFAP, an astrocyte marker that is elevated in the plasma following mTBI,[10] would be higher in APOE4 carriers compared to APOE4 non-carriers.

To test their hypothesis, the inventors recruited 60 young, currently-active, professional boxers and screened their blood for the presence of the APOE4 allele and levels of GFAP. They also used their recently develop mouse model of repeat mTBI to determine if acute and chronic outcome measures were affected by APOE status.[11]

Surprisingly, they found that the APOE4 allele is overrepresented in professional boxers. They also found, contrary to other findings for severe TBI, that pugilists with mTBI and having the APOE4 allele exhibit lower levels of plasma GFAP than non-carriers. Furthermore, the inventors found that APOE4 targeted replacement mice have faster arousal and ambulation times after single and repeat mTBI, and are resistant to acute synaptic changes following mTBI. However, APOE4 mice are not resistant to chronic white-matter inflammation induced by repetitive head injuries, as would have been expected if APOE4 were protective to mTBI sequelae as it now appears to be for acute mTBI effects.

The inventors concluded that while the APOE4 allele protects against the acute effect of mTBI, it worsens mTBI sequela, e.g., the symptoms or pathology of chronic neuroinflammation due to mTBI. This leads to the troubling scenario where APOE4 carriers may be enriched in sports (especially contact sports) and the military, as they suffer from fewer acute symptoms of mTBI. But without acute symptoms to signal the presence of a brain injury, the athlete or military member may continue to expose themselves to additional head trauma. In the long-term, these same athletes and military members are exposing themselves to a higher mTBI yield and are more susceptible to TBI sequelae such as chronic neuroinflammation.

Accordingly, the present invention provides an assay kit used to improve the assessment of mild traumatic brain injury, wherein the kit is configured to measure the presence or level of at least two biomarkers in a sample from the subject: APOE4 and GFAP. Also contemplated is a system or device capable of receiving the kit or a component thereof to detect the presence or measure the level of APOE4 and GFAP, said system being operatively associated with a computer, said computer having stored thereon a computer program which, when executed by said computer, causes the computer program to perform a method comprising correlating the presence or level of APOE4 and GFAP in the sample with an assessment of TBI in a subject.

The invention also includes a method of assessing TBI in a subject, comprising detecting APOE4 in a sample from the subject.

The invention also includes an ultrasensitive method for detecting GFAP and other biomarkers of TBI.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DETAILED DESCRIPTION OF THE INVENTION

Figure 1A:
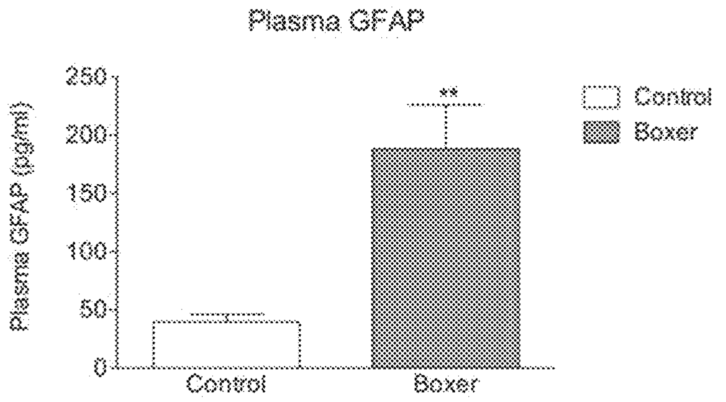
FIGS. 1A-B show that plasma GFAP is elevated in APOE4 negative, but not APOE4 positive, professional boxers compared to controls. A) Plasma GFAP levels in non-injured controls vs boxers. N=21 for controls, 28 for boxers. Unpaired t-test (=P<0.01). B) Plasma GFAP levels in boxers separated by the absence (−) or presence (+) of an APOE4 allele. N=21 for controls, 17 for E4 (−), 11 for E4 (+). One Way ANOVA with Newman-Keuls Multiple Comparisons Test; *=P<0.001 vs control; +=P<0.05 vs E4 (−).

Unless otherwise defined herein, scientific and technical terms used herein shall have the meanings that are commonly understood by those of ordinary skill in the art. Further, unless otherwise required by context, singular terms shall include pluralities and plural terms shall include the singular. The articles “a” and “an” are used herein to refer to one or to more than one (i.e., to at least one) of the grammatical object of the article. By way of example, “an element” means one element or more than one element.

In some embodiments, the invention includes an assay configured to determine or detect the presence or level of two or more biomarkers in a sample from a subject, wherein said two or more biomarkers comprise APOE4 and GFAP. The assay may be configured to assess traumatic brain injury (TBI), including mild TBI. It may be packaged as an APOE4 assay separate from a GFAP assay. The assay may be configured to determine the presence or level of APOE4 and the level of GFAP. The presence or level of APOE4 may be detected via an immunoassay or a nucleotide assay. The assay may be capable of measuring GFAP at a Lower Limit of Detection (LLOD) of less than about 500 femptograms/mL, such as about 0.1 to about 500 femtogram/mL, or less than about 300 fg/mL. such as about 150 fg/mL. The assay may be configured to perform a multiplexed immunoassay.

The two or more biomarkers being assayed may further comprise one, two, three, four, five, six, seven, eight, nine, ten, eleven, or all of tau, CKBB, IL-1β, IL-2, IL-6, IL-10, IL-22, IP-10, TNFα, TSLP, NFL (Neurofilament light chain), and NFH (Neurofilament heavy chain). The assay may be an ultrasensitive assay. The ultrasensitive assay may comprise in one or more vials, containers, or compartments: a. a surface comprising (i) a capture reagent for said biomarkers, said capture reagent bound to the surface, and (ii) an anchoring reagent bound to an anchoring oligonucleotide sequence, said anchoring reagent bound to the surface; b. a first detection reagent for said biomarkers that is linked to a first nucleic acid probe, wherein the first nucleic acid probe comprises an extended sequence that is complementary to the anchoring oligonucleotide sequence bound to the anchoring reagent; and c. a second detection reagent for said biomarkers that is linked to a second nucleic acid probe; wherein the kit is combined to form a proximity-based detection system, and the kit is configured to detect said biomarkers at a level below 500 femtogram/mL, preferably below 300 femtogram/mL, preferably below 100 femtogram/mL, preferably below 50 femtogram/mL, preferably below 25 femtogram/mL, preferably below 10 femtogram/mL.

In some embodiments, the invention includes a kit comprising the assay described above and in more detail below. The kit may comprise an assay module. It may comprise instructions for correlating the presence or level of APOE4 and GFAP in the sample with an assessment of TBI in the subject. The kit may comprise a GFAP calibrator composition or a GFAP control composition or both. The kit may comprise a computer readable medium having stored thereon a computer program that, when executed by a computer system, causes the computer system to perform a method comprising correlating the presence or level of APOE4 and GFAP in the sample with the presence of TBI in the subject.

The assay module may be multi-well assay plate comprising a plurality of assay wells used in an assay conducted in said kit. The assay plate comprises a plurality of assay domains and all or at least two of said assay domains comprises reagents for detecting or measuring APOE4 and GFAP. The assay module may be an assay cartridge. The assay cartridge may comprise a plurality of assay domains and all or at least two of said assay domains comprises reagents for detecting or measuring APOE4 and GFAP. The cartridge may comprise a flow cell having an inlet, an outlet or a detection chamber, and said inlet, detecting chamber, or outlet define a flow path through said flow cell, and said detection chamber is configured to measure said presence or said level of APOE4 and GFAP in said sample.

The kit may further comprise one or more additional assay reagents used in said assay, said one or more additional assay reagents provided in one or more vials, containers, or compartments of said kit. The kit may comprise an electrochemiluminescence (ECL) labeling reagent and the presence or the level of the biomarker is detected or measured in an assay conducted with said kit by detecting or measuring ECL.

The kit may comprise an additional kit component selected from one or more of (a) a bar-coded subject identification tag; (b) a dried blood spot collection card comprising a bar code; (c) a sample transport bag comprising desiccant; (d) a capillary with a plunger; or (e) a lancet.

In some embodiments, the invention includes an assay system capable of receiving the assay or kit described above, or a component of the kit such as an assay module, wherein the system is configured to detect the presence or level of APOE4 and GFAP and comprises an assay-plate-reading device operatively associated with a computer, said computer having stored thereon a computer program which, when executed by said computer, causes the computer program to perform a method comprising correlating the presence or level of the biomarkers with an assessment of TBI. The system may be configured to conduct an ECL measurement using the assay, the kit or the component.

In some embodiments, the invention includes a transitory or non-transitory computer readable medium having stored thereon a computer program which, when executed by a computer system operably connected to an assay system or assay-plate-reading device configured to detect or measure APOE4 and GFAP in a subject sample, causes the computer system to perform a method of assessing TBI, the method comprising determining whether the sample contains APOE4 and correlating the level of GFAP in the sample with the presence or absence of TBI.

In some embodiments, the method comprises determining whether the sample contains APOE4 and correlating the level of at least one additional biomarker in the sample with the presence or absence of TBI, wherein said at least one additional biomarker is selected from one, two, three, four, five, six, seven, eight, nine, ten, eleven, or all of GFAP, tau, CKBB, IL-1β, IL-2, IL-6, IL-10, IL-22, IP-10, TNFα, TSLP, NFL, and NFH.

In some embodiments, the invention incudes a method of assessing TBI, comprising detecting APOE4 in a subject who has experienced a potential traumatic brain injury. The method may comprise detecting APOE4 in a sample from said subject using an immunoassay or a nucleic acid assay. The method may further comprise subjecting the subject to one or more additional tests for TBI. The one or more tests may be selected from the group consisting of structural imaging, assessment of Glasgow Coma Scale, assessment of Abbreviated Injury Severity Scale, conducting an assay for GFAP, or combinations thereof. The one or more tests may comprise conducting an assay for GFAP. The method may comprise using the assay or kit or system or computer-readable medium described above and in more detail below. The method may further comprise subjecting the subject to a treatment for TBI.

In some embodiments, the invention is directed to a method of treating a subject for TBI, comprising the method of assessing TBI described above and in more detail below, and further comprising subjecting the subject to a treatment for TBI. The method of treatment may be rest, withdrawal from participating in an activity that has an increased likelihood of an additional TBI episode, withdrawal from or reduction of a reading activity, withdrawal from or reduction in a physical activity, reduction in a mentally-intensive activity, Goal Management Training (GMT), medications and combinations thereof.

The method of treatment may include determining the presence or degree of TBI, determining the susceptibility to TBI or TBI sequela, monitoring recovery from TBI, monitoring recovery from the sequelae of TBI, and preventing or minimizing TBI or TBI sequela. The method of treatment may also include monitoring improvements in memory, processing speed and inhibitory control/executive functioning. The contemplated methods may also include assessment of changes in neural, cognitive and biological markers resulting from treatment. The method of treatment may further include the inclusion of one or more medications to be used in combination with any of the foregoing treatment methods (e.g. determining the presence or degree of TBI). Contemplated medications include, but are not limited to: analgesics, anti-anxiety agents, anti-coagulants, anti-convulsants, anti-depressants, anti-psychotics, diuretics, muscle relaxants, sedative-hypnotic agents and/or stimulants. The medications for subjects with TBI are selected, prescribed and monitored by a physician and/or treatment team on an individual basis.

The subject may be a member of a group that has an increased likelihood of experiencing TBI. The subject may be APOE4 positive. The subject may be an active or former military personnel, public safety personnel, an American football player, a soccer player, a baseball player, a rugby player, a hockey player, a combat-sports participant, a race-car driver, a motorcycle racer, and a subject who has experienced a motor vehicle crash, fall, blow, or assault. The subject may not be suspected of having an expanding hematoma, a subarachnoid hemorrhage, a cerebral edema, raised intracranial pressure (ICP), or cerebral hypoxia.

In some embodiments, the invention includes a method of detecting APOE4 in a subject suspected of having or known to have TBI, comprising assaying for APOE4 in a sample from the subject. The subject may not be suspected of having an expanding hematoma, a subarachnoid hemorrhage, a cerebral edema, raised intracranial pressure (ICP), or cerebral hypoxia.

These methods of treatment or detection may comprise detecting APOE4 using a nucleotide assay or an immunoassay. These methods may comprise detecting the level of GFAP in the sample. These methods may comprise using the assay, kit, system, or computer readable medium described above and in more detail below.

In some embodiments, the invention includes an ultrasensitive assay for detecting GFAP in a sample from a subject, comprising, in one or more vials, containers, or compartments: a. a surface comprising (i) a capture reagent for GFAP, said capture reagent bound to the surface, and (ii) an anchoring reagent bound to an anchoring oligonucleotide sequence, said anchoring reagent bound to the surface; b. a first detection reagent for GFAP that is linked to a first nucleic acid probe, wherein the first nucleic acid probe comprises an extended sequence that is complementary to the anchoring oligonucleotide sequence bound to the anchoring reagent; and c. a second detection reagent for GFAP that is linked to a second nucleic acid probe; wherein the kit is combined to form a proximity-based detection system, and the kit is configured to detect GFAP at a level below 500 femtogram/mL, preferably below 300 femtogram/mL.

The assay is configured to detect GFAP at a Lower Limit of Detection (LLOD) of about 0.1 to about 500 femtogram/mL. The assay may be capable of detecting (e.g., configured to detect) GFAP at an LLOD of about 150 fg/mL, preferably below 100 femtogram/mL, preferably below 50 femtogram/mL, preferably below 25 femtogram/mL, preferably below 10 femtogram/mL. Such assays may be included in the kits, systems, and methods described above and below.

In some embodiments, the invention includes an ultrasensitive method for detecting other biomarkers of TBI, as discussed above and below. Such biomarkers include one, two, three, four, five, six, seven, eight, nine, ten, eleven, or more of tau, CKBB, IL-1β, IL-2, IL-6, IL-10, IL-22, IP-10, TNFα, TSLP, NFL, and NFH. It may be configured to assess traumatic brain injury. The assay may comprise, in one or more vials, containers, or compartments: a. a surface comprising (i) a capture reagent for said biomarkers, said capture reagent bound to the surface, and (ii) an anchoring reagent bound to an anchoring oligonucleotide sequence, said anchoring reagent bound to the surface; b. a first detection reagent for said biomarkers that is linked to a first nucleic acid probe, wherein the first nucleic acid probe comprises an extended sequence that is complementary to the anchoring oligonucleotide sequence bound to the anchoring reagent; and c. a second detection reagent for said biomarkers that is linked to a second nucleic acid probe; wherein the kit is combined to form a proximity-based detection system, and the kit is configured to detect said biomarkers at a level below 500 femtogram/mL, preferably below 300 femtogram/mL, preferably below 100 femtogram/mL, preferably below 50 femtogram/mL, preferably below 25 femtogram/mL, preferably below 10 femtogram/mL. Such assays may be included in the kits, systems, and methods described above and below.

As used herein, "traumatic brain injury" or "TBI" is caused by a traumatic incident (head being struck, head striking an object, or the brain undergoing an acceleration/deceleration movement (e.g., whiplash)) (including blast- and blunt-force causes) and means "a traumatically induced physiological disruption of brain function." TBI has been used interchangeably with "concussion" in the literature. Mild, moderate, and severe TBI are currently diagnosed by combinations of the criteria in Table A.

TABLE A

Criteria used to classify TBI severity

| Criteria | Mild | Moderate | Severe |
| --- | --- | --- | --- |
| Structural Imaging | Normal | Normal or abnormal | Normal or abnormal |
| Loss of Consciousness | <30 minutes | 30 minutes to 24 hours | >24 hours |
| Alteration of Consciousness/ Mental State | A moment to 24 hours | >24 hours | >24 hours |
| Post-traumatic Amnesia | 0-1 day | >1 and | 7 days |
| Glasgow Coma Scale (best available score in 24 hours) | 13-15 | 9-12 | 3-8 |
| Abbreviated Injury Severity Scale | 1-2 | 3 | 4-6 |

See Brasure M, et al., June 2012, cited in www.effectivehealthcare.ahrq.gov/reports/final.cfm.

As used herein, to "assess" TBI includes determining or detecting the presence of TBI or the degree of TBI or the susceptibility to TBI or TBI sequela, monitoring recovery from TBI, monitoring recovery from the sequelae of TBI, and preventing or minimizing TBI or TBI sequela.

As used herein, "TBI sequela" is any kind of secondary brain damage following an acute traumatic brain injury in a subject, and includes chronic brain damage, post-concussive disorder (PCD), severe chronic traumatic encephalopathy (CTE), late-life cognitive dysfunction, and cerebral vascular reactivity (CVR).

Metrics of TBI sequelae may be determined using the neurobehavioral symptom inventory (NSI), which is a validated metric for tracking outcomes after concussion in the military health system, the Ohio State University TBI Identification (OSU TBI-ID), the Sport Concussion Assessment Tool-3rd Edition (SCAT3), Glasgow Coma Scale (GCS), and the Glasgow Outcome Scale (GOS). Metrics of TBI sequelae also include an expanding hematoma, a subarachnoid hemorrhage, a cerebral edema, raised intracranial pressure (ICP), or cerebral hypoxia.

As used herein, "sample time" refers to the time between the traumatic event and the time at which the sample was collected. In a preferred embodiment, sample time for assessing TBI means the sample is collected from a subject within about 1-12, about 1-24, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24 hours, or about 1 or about 2 days after the traumatic injury. Such samples are preferably taken "early," i.e., within 24 hours. For example, UCH-L1 and CKBB are very early markers, usually decreasing to background within about 24 hours. In another preferred embodiment, sample time for assessing TBI is greater than about 1 day, e.g., about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32 days, or about 1, about 2, about 3, about 4, about 5, about 6, about 7, about 8, about 9, about 10, about 11, about 12, about 13, about 14, about 15, about 16, about 17 about, about 18 about, 19, about 20, about 21, about 22, about 23, about 24, about 48, about 51, about 52 weeks, or about 1, about 2, about 3, about 4, about 5, about 6, about 7, about 8, about 9, about 10, about 11, about 12, or about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, or about 50 years. In embodiments of assessing, e.g., in which a subject is monitored for recovery from acute TBI or the sequelae of TBI, sample time is preferably a combination of sample times over an extended period, which may be about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24 months, or about 2.5, about 3. About 4, about 5, about 6, about 7, about 8, about 9, about 10 years, or about 15, about 20, about 25, about 30, about 35, about 40 years.

Samples may be taken at these various sample times in some embodiments including when monitoring recovery from TBI, monitoring recovery from the sequelae of TBI, and preventing or minimizing TBI or TBI sequela.

The assay may be multiplexed, and may comprise an immunoassay and a nucleotide assay, or only an immunoassay. The assay may be configured to measure additional biomarkers that include ubiquitin carboxy-terminal hydrolase L1 (UCH-L1), creatinine kinase isoenzyme BB (CKBB), tau, p-tau, VILIP-1 (Visinin-Like Protein 1), MCP-1 (monocyte chemotactic protein 1; CCL2), vWF (von Willebrand Factor), S100 calcium-binding protein B (S100B), Platelet Derived Growth Factor Receptor Beta (PDGFRB), vascular endothelial growth factor (VEGF), all of which are increased in TBI compared to normal samples.

All APOE4 allele carriers who have experienced, or are members of a group that is likely to experience, traumatic brain injury are expected to benefit from the present inventions. Particular populations that will benefit include active and former military personnel, players of American football (e.g., high school, college, or professional players), soccer players, rugby players, baseball players (e.g., catchers), hockey players, combat-sports participants such as boxers (pugilists) MMA (mixed martial art) fighters, race-car drivers, motorcycle racers, and those who experience mTBI or other forms of TBI from motor vehicle collisions, falls, assault, etc. Subjects who particularly benefit from the methods of the invention include those who have sustained a traumatic event to the head but are negative on brain scans such as CT scans or MRI, as discussed above.

Subject who are not APOE4 carriers may also benefit from some aspects of the invention.

The samples that can be analyzed in the assays, kits, and methods of the invention include but are not limited to, any biological fluid, cell, tissue, organ and combinations or portions thereof, which includes or potentially includes a biomarker of a disease, disorder, or abnormality of interest. For example, a sample can be blood or blood fractions such as, blood pellet, serum, or plasma (EDTA or heparin); a histologic section of a specimen obtained by biopsy; or cells that are placed in or adapted to tissue culture. A sample further can be a subcellular fraction or extract, or a crude or substantially pure nucleic acid molecule or protein preparation. Other suitable samples include biopsy tissue, intestinal mucosa, urine, parotid gland, hematological tissues, intestine, liver, pancreas, or nervous system. The sample can be taken from any subject, including but not limited to animals, mammals, primates, non-human primates, humans, and the like. The biomarkers disclosed herein may be used immediately after the traumatic injury, at some point after the injury, and/or and throughout the course recovery or treatment.

Additional biomarkers that may be measured include UCH-L1, CKBB, tau, p-tau, VILIP-1, MCP-1, VWF, S100B, PDGFRβ, and VEGF.

One of average skill in the art of biological assays will be aware of numerous suitable approaches and instrumentation for measuring the biomarkers and biomarker panels of the invention. In one embodiment, the kit is configured to measure biomarker levels using an immunoassay or a nucleic acid assay or both. In a preferred embodiment, the kit includes a multi-well assay plate comprising a plurality of assay wells configured to measure the level of said plurality of biomarkers in one or more samples. Preferably, the wells are configured to enable the use of individual wells to conduct multiplexed measurements of a plurality of different biomarkers. In one such assay plate, a well of the assay plate includes a plurality of assay domains, at least two of the assay domains comprising reagents for measuring different biomarkers. In an alternative preferred embodiment, the kit includes an assay cartridge to measure biomarkers in a sample. Preferably, the cartridge comprises a flow cell having an inlet, an outlet and a detection chamber, said inlet, detecting chamber, and outlet defining a flow path through said flow cell, said detection chamber configured to measure said level of said plurality of biomarkers in said sample. In some embodiments, the kit includes particles such as microspheres.

Kits used in the present method can further include one or more additional assay reagents used in an assay and those additional reagents can be provided in one or more vials, containers, or compartments of a kit. The kit can also include (a) a bar-coded subject identification tag; (b) a dried blood spot collection card comprising a bar code that for example, can be used to facilitate sample identification; (c) a sample transport bag comprising desiccant; (d) a capillary with a plunger; and/or (e) a lancet.

As used herein, a "biomarker" is a substance that is associated with a particular biological state, which can be a disease or abnormal condition. A change in the levels of a biomarker can correlate with the risk or progression of a disease or abnormality or with the susceptibility of the disease or abnormality to a given treatment. A biomarker can be useful in the diagnosis of disease risk or the presence of disease in an individual, or to tailor treatments for the disease in an individual (choices of drug treatment or administration regimes). In evaluating potential therapies, e.g., drug therapies, a biomarker can be used as a surrogate for a natural endpoint such as survival or irreversible morbidity. If a treatment alters a biomarker that has a direct connection to improved health, the biomarker serves as a "surrogate endpoint" for evaluating clinical benefit.

As used herein, the term "level" refers to the amount, concentration, or activity of a biomarker. The term "level" can also refer to the rate of change of the amount, concentration or activity of a biomarker. A level can be represented, for example, by the amount or synthesis rate of messenger RNA (mRNA) encoded by a gene, the amount or synthesis rate of polypeptide corresponding to a given amino acid sequence encoded by a gene, or the amount or synthesis rate of a biochemical form of a biomarker accumulated in a cell, including, for example, the amount of particular post-synthetic modifications of a biomarker such as a polypeptide, nucleic acid or small molecule. The term can be used to refer to an absolute amount of a biomarker in a sample or to a relative amount of the biomarker, including amount or concentration determined under steady-state or non-steady-state conditions. Level can also refer to an assay signal that correlates with the amount, concentration, activity or rate of change of a biomarker. The level of a biomarker can be determined relative to a control marker in a sample.

Specific biomarkers valuable in distinguishing between normal and injured subjects can be identified by visual inspection of the data, for example, by visual classification of data plotted on a one-dimensional or multidimensional graph, or by using statistical methods such as characterizing the statistically weighted difference between control individuals and diseased subjects and/or by using Receiver Operating Characteristic (ROC) curve analysis. A variety of suitable methods for identifying useful biomarkers and setting detection thresholds/algorithms are known in the art and will be apparent to the skilled artisan.

For example and without limitation, diagnostically valuable biomarkers can be first identified using a statistically weighted difference between control individuals and TBI subjects, calculated as $$\frac{D-N}{\sqrt{\sigma_D * \sigma_N}}$$

wherein D is the median level of a biomarker in subjects diagnosed as having been exposed traumatic brain event, N is the median (or average) of the control individuals, OD is the standard deviation of D and ON is the standard deviation of N. The larger the magnitude, the greater the statistical difference between the diseased and normal populations.

According to one embodiment of the invention, biomarkers resulting in a statistically weighted difference between control individuals and TBI subjects of greater than, e.g., 1, 1.5, 2, 2.5 or 3 could be identified as diagnostically valuable markers to predict the severity of the injury.

Another method of statistical analysis for identifying biomarkers is the use of z-scores, e.g., as described in Skates et al. (2007) Cancer Epidemiol. Biomarkers Prev. 16(2):334-341.

Another method of statistical analysis that can be useful in the inventive methods of the invention for determining the efficacy of particular candidate analytes, such as particular biomarkers, for acting as diagnostic marker(s) is ROC curve analysis. An ROC curve is a graphical approach to looking at the effect of a cut-off criterion, e.g., a cut-off value for a diagnostic indicator such as an assay signal or the level of an analyte in a sample, on the ability of a diagnostic to correctly identify positive or negative samples or subjects. One axis of the ROC curve is the true positive rate (TPR, i.e., the probability that a true positive sample/subject will be correctly identified as positive, or alternatively, the false negative rate (FNR=1-TPR, the probability that a true positive sample/subject will be incorrectly identified as a negative). The other axis is the true negative rate, i.e., TNR, the probability that a true negative sample will be correctly identified as a negative, or alternatively, the false positive rate (FPR=1-TNR, the probability that a true negative sample will be incorrectly identified as positive). The ROC curve is generated using assay results for a population of samples/subjects by varying the diagnostic cut-off value used to identify samples/subjects as positive or negative and plotting calculated values of TPR or FNR and TNR or FPR for each cut-off value. The area under the ROC curve (referred to herein as the AUC) is one indication of the ability of the diagnostic to separate positive and negative samples/subjects. In one embodiment, a biomarker provides an AUC≥0.7. In another embodiment, a biomarker provides an AUC≥0.8. In another embodiment, a biomarker provides an AUC≥0.9.

Diagnostic indicators analyzed by ROC curve analysis can be a level of an analyte, e.g., a biomarker, or an assay signal. Alternatively, the diagnostic indicator can be a function of multiple measured values, for example, a function of the level/assay signal of a plurality of analytes, e.g., a plurality of biomarkers, or a function that combines the level or assay signal of one or more analytes with a subject's scoring value that is determined based on visual, radiological and/or histological evaluation of a subject. The multiparameter analysis can provide more accurate diagnosis relative to analysis of a single marker.

Candidates for a multi-analyte panel could be selected by using criteria such as individual analyte ROC areas, median difference between groups normalized by geometric interquartile range (IQR) etc. The objective is to partition the analyte space to improve separation between groups (for example, normal and disease populations) or to minimize the misclassification rate.

One approach is to define a panel response as a weighted combination of the response for the individual analytes and then compute an objective function like ROC area, product of sensitivity and specificity, etc. See e.g., WO 2004/058055, as well as US2006/0205012, the disclosures of which are incorporated herein by reference in their entireties. The weighting coefficients define the partitioning object; for linear combinations the object is a line in 2 dimensions, a plane in 3 dimensions and a hyperplane in higher dimensions. The optimal coefficients maximize the objective function and can be determined using algorithms for finding function extrema in multiple dimensions, e.g., gradient descent methods, downhill simplex methods, simulated annealing and the like; more details can be found in "Numerical Recipes in C, The Art of Scientific Computing", W. Press et al., Cambridge University Press, 1992.

Another approach is to use discriminant analysis, where a multivariate probability distribution (normal, multinomial etc.) is used to describe each group. Several distributions result in partitioning hyperplanes in analyte space. One advantage of this approach is the ability to classify measurements into multiple groups (e.g. normal, disease 1, disease 2) simultaneously, rather than two at a time. For further details, see "Principles of Multivariate Analysis, A User's Perspective", W. J. Krzanowski, Oxford University Press, 2000 and "Multivariate Observations", G. A. F. Seber, John Wiley, 2004.

Once the partitioning hyperplanes have been determined, the robustness of different assay panels can be compared by evaluating a distance metric to the separating hyperplanes for each group. It is noteworthy that the algorithms described above are designed to find the best classification between groups; therefore these algorithms can also be used to distinguish between different diseases or populations or subgroups of the same disease or population. Finally, categorical data (age, gender, race, ethnicity, etc.) can also be coded into different levels and used as an optimizing variable in this process.

All or one or more parts of the algorithm(s) and statistical method(s) disclosed herein can be performed by or executed on a processor, general purpose or special purpose or other such machines, integrated circuits or by any combination thereof. Moreover, the software instructions for performing the algorithm(s) and statistical methods(s) disclosed herein may also be stored in whole or in part on a computer-readable medium, i.e., a storage device for use by a computer, processor, general or special purpose or other such machines, integrated circuits or by any combination thereof. A non-limiting list of suitable storage devices includes but is not limited to a computer hard drive, compact disk, transitory propagating signals, nontransitory medium, a network, or a portable media device to be read by an appropriate drive or via an appropriate connection.

As used herein "Goal Management Training (GMT)" refers to a cognitive remediation protocol for the treatment of TBI that can be applied to subjects afflicted with a TBI such as military members, veterans, public safety personnel, an American football player, a soccer player, a baseball player, a rugby player, a hockey player, a combat-sports participant, a race-car driver, a motorcycle racer, and a subject who has experienced a motor vehicle crash, fall, blow, or assault.

Biomarker presence can be detected and biomarker levels can be measured using any of a number of techniques available to the person of ordinary skill in the art, e.g., direct physical measurements (e.g., mass spectrometry) or binding assays (e.g., nucleic acid assays, immunoassays, agglutination assays and immunochromatographic assays). Biomarkers identified herein can be detected or measured by any suitable immunoassay method, including but not limited to, ELISA, microsphere-based immunoassay methods, lateral flow test strips, antibody based dot blots, western blots, or particle-based immunoassays and nucleic acid assays. The method can also comprise detecting or measuring a signal that results from a chemical reaction, e.g., a change in optical absorbance, a change in fluorescence, the generation of chemiluminescence or electrochemiluminescence, a change in reflectivity, refractive index or light scattering, the accumulation or release of detectable labels from the surface, the oxidation or reduction or redox species, an electrical current or potential, changes in magnetic fields, etc. Suitable detection techniques can detect binding events by measuring the participation of labeled binding reagents through the measurement of the labels via their photoluminescence (e.g., via measurement of fluorescence, time-resolved fluorescence, evanescent wave fluorescence, up-converting phosphors, multi-photon fluorescence, etc.), chemiluminescence, electrochemiluminescence, light scattering, optical absorbance, radioactivity, magnetic fields, enzymatic activity (e.g., by measuring enzyme activity through enzymatic reactions that cause changes in optical absorbance or fluorescence or cause the emission of chemiluminescence). Alternatively, detection techniques can be used that do not require the use of labels, e.g., techniques based on measuring mass (e.g., surface acoustic wave measurements), refractive index (e.g., surface plasmon resonance measurements), or the inherent luminescence of an analyte.

Nucleic acid assays useful in the invention include PCR (Polymerase Chain Reaction), LCR (Ligase Chain Reaction), SDA (Strand Displacement Amplification), 3SR (Self-Sustained Synthetic Reaction), and isothermal amplification methods (e.g., helicase-dependent amplification or rolling circle amplification (RCA)).

Binding assays for measuring biomarker levels or detecting biomarkers can use solid phase or homogenous formats. Suitable assay methods include sandwich or competitive binding assays. Examples of sandwich immunoassays are described in U.S. Pat. Nos. 4,168,146 and 4,366,241, both of which are incorporated herein by reference in their entireties. Examples of competitive immunoassays include those disclosed in U.S. Pat. Nos. 4,235,601, 4,442,204 and 5,208,535, each of which are incorporated herein by reference in their entireties.

Multiple biomarkers can be measured or detected using a multiplexed assay format, e.g., multiplexing through the use of binding reagent arrays, multiplexing using spectral discrimination of labels, multiplexing of flow cytometric analysis of binding assays carried out on particles, e.g., using the Luminex® system. Suitable multiplexing methods include array based binding assays using patterned arrays of immobilized antibodies directed against the biomarkers of interest. Various approaches for conducting multiplexed assays have been described (See e.g., US 20040022677; US 20050052646; US 20030207290; US 20030113713; US 20050142033; and US 20040189311, each of which is incorporated herein by reference in their entireties.

One approach to multiplexing binding assays involves the use of patterned arrays of binding reagents, e.g., U.S. Pat. Nos. 5,807,522 and 6,110,426; Delehanty J-B., Printing functional protein microarrays using piezoelectric capillaries, Methods Mol. Bio. (2004) 278: 135-44; Lue R Y et al., Site-specific immobilization of biotinylated proteins for protein microarray analysis, Methods Mol. Biol. (2004) 278: 85-100; Lovett, Toxicogenomics: Toxicologists Brace for Genomics Revolution, Science (2000) 289: 536-537; Berns A, Cancer: Gene expression in diagnosis, nature (2000), 403, 491-92; Walt, Molecular Biology: Bead-based Fiber-Optic Arrays, Science (2000) 287: 451-52 for more details). Another approach involves the use of binding reagents coated on beads that can be individually identified and interrogated. See e.g., WO 9926067, which describes the use of magnetic particles that vary in size to assay multiple analytes; particles belonging to different distinct size ranges are used to assay different analytes. The particles are designed to be distinguished and individually interrogated by flow cytometry. Vignali has described a multiplex binding assay in which 64 different bead sets of microparticles are employed, each having a uniform and distinct proportion of two dyes (Vignali, D. A A, "Multiplexed Particle-Based Flow Cytometric Assays" J. ImmunoL Meth. (2000) 243: 243-55). A similar approach involving a set of 15 different beads of differing size and fluorescence has been disclosed as useful for simultaneous typing of multiple pneumococcal serotypes (Park, M. K et al., "A Latex Bead-Based Flow Cytometric Immunoassay Capable of Simultaneous Typing of Multiple Pneumococcal Serotypes (Multibead Assay)" Clin. Diag. Lab ImmunoL (2000) 7: 4869). Bishop, J E et al. have described a multiplex sandwich assay for simultaneous quantification of six human cytokines (Bishop, L E. et al., "Simultaneous Quantification of Six Human Cytokines in a Single Sample Using Microparticle-based Flow Cytometric Technology," Clin. Chem (1999) 45:1693-1694).

A test for assessing TBI, e.g., a diagnostic test, can be conducted in a single assay chamber, such as a single well of an assay plate or an assay chamber of a cartridge. The assay modules, e.g., assay plates or cartridges or multi-well assay plates, and methods and apparatuses for conducting assay measurements suitable for the present invention are described for example, in US 2004/0022677; US 2005/0052646; US 2005/0142033; US 2004/0189311; U.S. Pat. No. 6,977,772; US 2011/0201099, each of which is incorporated herein by reference in its entirety for all purposes. Assay plates and plate readers are commercially available (MULTI-SPOT® and MULTI-ARRAY® plates, SECTOR® and other instruments, MESO SCALE DISCOVERY, a division of Meso Scale Diagnostics, LLC., Rockville, MD).

Ultrasensitive Assays

In some embodiments, the invention is directed to an ultrasensitive assay for measuring certain biomarkers that are altered in TBI. These markers include GFAP, tau, CKBB, IL-1β, IL-2, IL-6, IL-10, IL-22, IP-10, TNFα, and TSLP, and brain biomarkers (Neurofilament light chain) NFL, (Neurofilament heavy chain) NFH.

Most of the papers where GFAP clinical data are reported are unable to detect the levels in healthy individuals, as shown in Table 1.

TABLE 1

Reported human GFAP levels in healthy individuals

| Source | GFAP level range pg/mL | Assay type used | Assay LOD pg/mL | # donors | # donors with detectable levels |
|---|---|---|---|---|---|
| Clinical Chemistry 58, No. 1, 2012 | 70 (average) | ECL (Elecsys) | 50 | 132 | NA |
| Clinical Chemistry 45, No. 1, 1999 | 2-49 | DELFIA | <10 | 70 | 10 |
| Critical Care (2015) 19: 362 | 48-76 | ELISA | 45 | 135 | 12 |
| American Journal of Hematology, Vol. 86: 427 (2011) | 70 ± 80 | ECL (MSD) | 11 | 60 | NA |
| Quanterix Poster TBI research symposium 2015 | 0.3-20 | Simoa | NA | 28 | 28 |

Thus, it would be important to use an assay that is more sensitive than existing assays for measuring GFAP for some embodiments of the present invention, such as detecting GFAP, and monitoring TBI treatment or TBI sequelae. The present invention provides for such an ultrasensitive assay, as shown in Tables 2 and 3.

TABLE 2

Ultrasensitive Assay's performance

| | GFAP |
|---|---|
| Calibration Range | 900,000-19 fg/mL |
| Limit of Detection | 150 fg/mL |
| Estimated Lower Limit of Quantitation | 700 fg/mL |
| Estimated Upper Limit of Quantitation | 1170 pg/mL |

TABLE 3

The Ultrasensitive Assay detects measurable GFAP in 100% of normal samples tested

| | |
|---|---|
| Median concentration (10 serum samples from apparently healthy donors) | 36 pg/mL |
| Median concentration (10 plasma samples from apparently healthy donors) | 37 pg/mL |
| Mean concentration (10 serum samples from apparently healthy donors) | 39 pg/mL |
| Mean concentration (14 plasma samples from apparently healthy donors) | 42 pg/mL |
| Percentage of normal serum/plasma within assay range (14 samples each) | 100% |

Preferably, the ultrasensitive assay has a lower limit of detection (LLOD) of less than about 100, about 90, about 80, about 70, about 60, about 50, about 40, about 30, about 20, about 10, about 1, or about 0.1 pg/ml. More specifically, the assay has a LLOD of less than about 200, 175, 150, 125, 100, 75, 50, 25, or 10 fg/mL for GFAP, tau, CKBB, IL-1β, IL-2, IL-6, IL-10, IL-22, IP-10, TNFα, and TSLP, and brain biomarkers (Neurofilament light chain) NFL, (Neurofilament heavy chain) NFH, or the other biomarkers discussed above. Specific embodiments include combinations of GFAP and tau; GFAP and CKBB; and GFAP, tau, and CKBB. GFAP and tau are more useful than GFAP alone, and CKBB is particularly useful as a very early marker, and in boxers. In embodiments that include determining or detecting APOE4 in a patient, measuring the level of GFAP is especially useful. Using an ultrasensitive assay enables the detection of very low levels of markers such as GFAP that may reflect very mild TBI in APOE4 carriers and residual brain damage in all subjects recovering from TBI (including mTBI) and the sequelae thereof, in both APOE3 and APOE4 subjects. For example, the LLOD of GFAP in plasma using standard immunoassays is about 50 pg/ml.

The present invention contemplates the following specific embodiments. Various modifications, additions and alterations may be made to embodiments described herein by one skilled in the art without departing from the spirit and scope of the invention. Such modifications, additions, and alterations are intended to fall within the scope of the claims. The disclosures of US 2014/0272939 and WO 2015/175856 are herein incorporated by reference in their entirety for all purposes.

Embodiment (1): a method of detecting an analyte of interest in a sample comprising: binding the analyte to: (i) a capture reagent on a surface that comprises the capture reagent for the analyte and an anchoring reagent; and (ii) a detection reagent for the analyte that is linked to a nucleic acid probe; thereby forming a complex on the surface comprising the capture reagent, the analyte, and the detection reagent; extending the probe to form an extended sequence comprising an anchoring region that binds the anchoring reagent; binding the extended sequence to the anchoring reagent; and measuring the amount of extended sequence bound to the surface.

In embodiment (1), the capture reagent can be an antibody, antigen, ligand, receptor, oligonucleotide, hapten, epitope, mimitope, or an aptamer. In a specific embodiment, the capture reagent is an antibody. The detection reagent can be an antibody, antigen, ligand, receptor, oligonucleotide, hapten, epitope, mimitope, or an aptamer, and in a specific embodiment, the detection reagent is an antibody. In one specific example of embodiment (1), the capture and detection reagents are antibodies to the analyte. The anchoring reagent can include an oligonucleotide sequence, aptamer, aptamer ligand, antibody, antigen, ligand, receptor, hapten, epitope, or a mimetope; and optionally, the anchoring region can include an aptamer and the anchoring reagent can include an aptamer ligand. The anchoring region can comprise a nucleic acid sequence and the anchoring reagent can include a DNA-binding protein. The anchoring region can include an oligonucleotide sequence and the anchoring reagent can include a complementary oligonucleotide sequence. The anchoring region can include a single stranded oligonucleotide sequence or a double stranded oligonucleotide sequence.

The binding step of embodiment (1) can further include forming a triple helix between the anchoring region and the anchoring reagent. The method can also further comprise denaturing the anchoring region to expose a single stranded sequence prior to the binding step; exposing the anchoring region to helicase activity prior to the binding step; and/or exposing the anchoring region to nuclease treatment prior to the binding step. In this embodiment, the anchoring region can comprise one or more hapten-modified bases and the anchoring reagent can include one or more antibodies specific for the hapten; and/or the anchoring region can include one or more ligand-modified bases and the anchoring reagent can include one or more receptors specific for the ligand. The extended sequence can further comprise one or more detection sequences and the measuring step can include contacting the extended sequence with a plurality of labeled probes complementary to the one or more detection sequences; the extended sequence can include one or more modified bases and the measuring step can include contacting the extended sequence with a plurality of detectable moieties capable of binding to the one or more modified bases; and/or the extended sequence can comprise one or more labeled bases and the measuring step can further include detecting the presence of the one or more labeled bases. In this embodiment, the one or more modified bases comprise an aptamer, aptamer ligand, antibody, antigen, ligand, receptor, hapten, epitope, or a mimetope and the plurality of detectable moieties each comprise a binding partner of the one or more modified bases and a detectable label. The one or more modified bases can comprise streptavidin and the plurality of detectable moieties each comprise biotin and a detectable label; and/or the one or more modified bases can comprise biotin and the plurality of detectable moieties each comprise streptavidin and a detectable label; and/or the one or more modified bases can comprise avidin and the plurality of detectable moieties each comprise biotin and a detectable label; and/or the one or more modified bases can comprise biotin and the plurality of detectable moieties each comprise avidin and a detectable label.

The first step of embodiment (1) can comprise binding the analyte to the following species in the following order: (i) the capture reagent on a surface; and (ii) the detection reagent for the analyte; or the first step of embodiment (1) can comprise binding the analyte to the following species in the following order: (i) the detection reagent for the analyte; and (ii) the capture reagent on the surface; and/or the first step can comprise binding the analyte to the following species simultaneously or substantially simultaneously: (i) the capture reagent on a surface; and (ii) the detection reagent for the analyte.

The extending step of embodiment (1) can comprise binding the probe to a template nucleic acid sequence and extending the probe by polymerase chain reaction; and/or binding the probe to a template nucleic acid sequence, forming a circular nucleic acid template, and extending the circular template by rolling circle amplification. In this embodiment, the extended probe can remain localized on the surface following probe extension. Therefore, the complex can remain bound to the surface after the extending step, e.g., the extended probe is bound to the anchoring reagent at a position within 10-100 μm of the location of the complex on the surface.

The extending step of embodiment (1) can comprise PCR (Polymerase Chain Reaction), LCR (Ligase Chain Reaction), SDA (Strand Displacement Amplification), 3SR (Self-Sustained Synthetic Reaction), or isothermal amplification methods. In one embodiment, the extending step can include isothermal amplification methods, e.g., helicase-dependent amplification or rolling circle amplification (RCA).

The surface referenced in embodiment (1) can comprise a particle and/or an assay domain of an assay module such as a well of a multi-well plate or an assay chamber of a cartridge. The surface can comprise a plurality of distinct binding domains and the capture reagent and the anchoring reagent are located on two distinct binding domains on the surface. If the surface is a well of a plate, the well can comprise a plurality of distinct binding domains and the capture reagent and the anchoring reagent are located on two distinct binding domains within the well; and/or the surface can include a plurality of distinct binding domains and the capture reagent and the anchoring reagent are located on the same binding domain on the surface. In one embodiment, the well can include a plurality of distinct binding domains and the capture reagent and the anchoring reagent are located on the same binding domain within the well. The capture reagent and the anchoring reagent may be within 10-100 nm on the surface. The surface can include an electrode and the measuring step further can include applying a voltage waveform to the electrode to generate an electrochemiluminesce signal, and optionally, the method includes collecting the particle on an electrode and applying a voltage waveform to the electrode to generate an electrochemiluminescence signal.

The measuring step of embodiment (1) can further comprise binding the extended sequence to a detection probe having a detectable label, measuring the detectable label and correlating the measurement to the amount of analyte in the sample, wherein the detection probe comprising a nucleic acid sequence that is complementary to a region of the extended sequence. The detectable label can be measured by a measurement of light scattering, optical absorbance, fluorescence, chemiluminescence, electrochemiluminescence, bioluminescence, phosphorescence, radioactivity, magnetic field, or combinations thereof. In a particular example of embodiment (1), the detectable label is an ECL label and the measuring step can include measuring an ECL signal.

Embodiment (2): a kit for the detection of an analyte of interest in a sample comprising, in one or more vials, containers, or compartments: (a) a surface comprising (i) a capture reagent for the analyte, and (ii) an anchoring reagent; and (b) a detection reagent for the analyte that is linked to a nucleic acid probe.

The anchoring reagent of embodiment (2) can comprise an oligonucleotide sequence, aptamer, aptamer ligand, antibody, antigen, ligand, receptor, hapten, epitope, or a mimetope, and the capture reagent can comprise an antibody, antigen, ligand, receptor, oligonucleotide, hapten, epitope, mimitope, or aptamer. In a particular embodiment, the capture reagent can include an antibody and/or the detection reagent can include an antibody, antigen, ligand, receptor, oligonucleotide, hapten, epitope, mimitope, or aptamer. In a specific embodiment of the kit, the detection reagent is an antibody.

The surface of the kit of embodiment (2) can include a particle and/or an assay domain of an assay module such as a well of a multi-well plate or an assay chamber of a cartridge. The surface can comprise a plurality of distinct binding domains and the capture reagent and the anchoring reagent are located on two distinct binding domains on the surface. If the surface of the kit is a well of a plate, the surface can comprise a plurality of distinct binding domains and the capture reagent and the anchoring reagent are located on two distinct binding domains within the well; and/or the surface can include a plurality of distinct binding domains and the capture reagent and the anchoring reagent are located on the same binding domain on the surface. In a particular example of the kit, the surface is a well and the well can include a plurality of distinct binding domains and the capture reagent and the anchoring reagent are located on the same binding domain within the well. The capture reagent and the anchoring reagent can be within 10-100 nm on the surface. Moreover, the surface of the kit can comprise an electrode.

Embodiment (3): a method of detecting an analyte of interest in a sample comprising: (a) binding the analyte to: (i) a capture reagent on a surface that comprises the capture reagent for the analyte and an anchoring reagent comprising an anchoring oligonucleotide sequence; and (ii) a detection reagent for the analyte that is linked to a nucleic acid probe; thereby forming a complex on the surface comprising the capture reagent, the analyte, and the detection reagent; (b) extending the probe to form an extended sequence comprising an anchoring sequence complement that is complementary to the anchoring sequence; (c) hybridizing the anchoring sequence to the anchoring sequence complement; and (d) measuring the amount of extended sequence bound to the surface.

In embodiment (3), the capture reagent can be an antibody, antigen, ligand, receptor, oligonucleotide, hapten, epitope, mimitope, or an aptamer, and in a particular example, the capture reagent is an antibody. Likewise, the detection reagent is an antibody, antigen, ligand, receptor, oligonucleotide, hapten, epitope, mimitope, or an aptamer, and in a particular example of embodiment (3), the detection reagent is an antibody. In one example of embodiment (3), the capture and detection reagents are antibodies to the analyte. The anchoring oligonucleotide sequence can comprise a single stranded oligonucleotide sequence or a double stranded oligonucleotide sequence. The extended sequence may further comprise one or more detection sequences and the measuring step further can include contacting the extended sequence with a plurality of labeled probes complementary to the one or more detection sequences; alternatively or additionally, the extended sequence further can include one or more modified bases and the measuring step further can include contacting the extended sequence with a plurality of detectable moieties capable of binding to the one or more modified bases. In a particular example, the extended sequence further can include one or more labeled bases and the measuring step further can include detecting the presence of the one or more labeled bases. The one or more modified bases can comprise an aptamer, aptamer ligand, antibody, antigen, ligand, receptor, hapten, epitope, or a mimetope and the plurality of detectable moieties each comprise a binding partner of the one or more modified bases and a detectable label. The one or more modified bases can comprise streptavidin and the plurality of detectable moieties each comprise biotin and a detectable label; the one or more modified bases comprise biotin and the plurality of detectable moieties each comprise streptavidin and a detectable label; the one or more modified bases comprise avidin and the plurality of detectable moieties each comprise biotin and a detectable label; and/or the one or more modified bases comprise biotin and the plurality of detectable moieties each comprise avidin and a detectable label.

Step (a) of embodiment (3) can include binding the analyte to the following species in the following order: (i) the capture reagent on a surface; and (ii) the detection reagent for the analyte. Alternatively, step (a) can include binding the analyte to the following species in the following order: (i) the detection reagent for the analyte; and (ii) the capture reagent on the surface. In yet another example, step (a) can include binding the analyte to the following species simultaneously or substantially simultaneously: (i) the capture reagent on a surface; and (ii) the detection reagent for the analyte.

The extending step of embodiment (3) can include binding the probe to a template nucleic acid sequence and extending the probe by polymerase chain reaction. Alternatively, the extending step can include binding the probe to a template nucleic acid sequence, forming a circular nucleic acid template, and extending the circular template by rolling circle amplification. The extended probe can remain localized on the surface following probe extension, e.g., the complex remains bound to the surface after the extending step. In one example, the extended probe is bound to the anchoring reagent at a position within 10-100 μm of the location of the complex on the surface. In this particular embodiment, the extending step can include PCR (Polymerase Chain Reaction), LCR (Ligase Chain Reaction), SDA (Strand Displacement Amplification), 3SR (Self-Sustained Synthetic Reaction), or isothermal amplification methods. For example, the extending step can include isothermal amplification methods, e.g., helicase-dependent amplification or rolling circle amplification (RCA).

The surface of embodiment (3) can comprise a particle and/or an assay domain of an assay module such as a well of a multi-well plate or an assay chamber of a cartridge. The surface can comprise a plurality of distinct binding domains and the capture reagent and the anchoring reagent are located on two distinct binding domains on the surface. If the surface is a well of a plate, it can comprise a plurality of distinct binding domains and the capture reagent and the anchoring reagent are located on two distinct binding domains within the well. The surface can comprise a plurality of distinct binding domains and the capture reagent and the anchoring reagent are located on the same binding domain on the surface. If the surface is a well, it can comprise a plurality of distinct binding domains and the capture reagent and the anchoring reagent are located on the same binding domain within the well. The capture reagent and the anchoring reagent can be within 10-100 nm on the surface. In a particular example, the surface can include an electrode and the measuring step further can include applying a voltage waveform to the electrode to generate an electrochemiluminesce signal. The method can further include collecting the particle on an electrode and applying a voltage waveform to the electrode to generate an electrochemiluminescence signal. The measuring step can further comprise binding the extended sequence to a detection probe having a detectable label, measuring the detectable label and correlating the measurement to the amount of analyte in the sample, wherein the detection probe comprising a nucleic acid sequence that is complementary to a region of the extended sequence. In this embodiment, the detectable label is measured by a measurement of light scattering, optical absorbance, fluorescence, chemiluminescence, electrochemilumin-escence, bioluminescence, phosphorescence, radioactivity, magnetic field, or combinations thereof. For example, the detectable label is an ECL label and the measuring step can include measuring an ECL signal.

Embodiment (4): a kit for the detection of an analyte of interest in a sample comprising, in one or more vials, containers, or compartments: (a) a surface comprising (i) a capture reagent for the analyte, and (ii) an anchoring reagent comprising an anchoring oligonucleotide sequence; and (b) a detection reagent for the analyte that is linked to a nucleic acid probe.

The kit of embodiment (4) includes a capture reagent comprising an antibody, antigen, ligand, receptor, oligonucleotide, hapten, epitope, mimitope, or aptamer. In a specific example, the capture reagent can include an antibody. Likewise, the detection reagent can include an antibody, antigen, ligand, receptor, oligonucleotide, hapten, epitope, mimitope, or aptamer, and particularly, the detection reagent can include an antibody.

The kit of embodiment (4) includes a surface that can comprise a particle and/or an assay domain of an assay module such as a well of a multi-well plate or an assay chamber of a cartridge. The surface can include a plurality of distinct binding domains and the capture reagent and the anchoring reagent are located on two distinct binding domains on the surface. If the surface is a well, the well can include a plurality of distinct binding domains and the capture reagent and the anchoring reagent are located on two distinct binding domains within the well. The surface can comprise a plurality of distinct binding domains and the capture reagent and the anchoring reagent are located on the same binding domain on the surface, e.g., if the surface is a well, the well can include a plurality of distinct binding domains and the capture reagent and the anchoring reagent are located on the same binding domain within the well. For example, the capture reagent and the anchoring reagent are within 10-100 nm on the surface. The surface of embodiment (4) can include an electrode.

Embodiment (5): a method of detecting an analyte of interest in a sample comprising: (a) binding the analyte to: (i) a capture reagent on a surface that comprises the capture reagent for the analyte and an anchoring reagent comprising an anchoring oligonucleotide sequence; (ii) a first detection reagent for the analyte that is linked to a first nucleic acid probe; and (iii) a second detection reagent for the analyte that is linked to a second nucleic acid probe; thereby forming a complex on the surface comprising the binding reagent, the analyte, and the first and second detection reagents; (b) using an extension process that requires the first and second probes to be in proximity, extending the second probe to form an extended sequence comprising an anchoring sequence complement that is complementary to the anchoring sequence; (c) hybridizing the anchoring sequence to the anchoring sequence complement; and (d) measuring the amount of extended sequence bound to the surface.

The capture reagent of embodiment (5) can be an antibody, antigen, ligand, receptor, oligonucleotide, hapten, epitope, mimitope, or an aptamer. In a specific example, the capture reagent is an antibody. Likewise, the first detection reagent is an antibody, antigen, ligand, receptor, oligonucleotide, hapten, epitope, mimitope, or an aptamer, and in a particular example, the first detection reagent is an antibody. The second detection reagent can be an antibody, antigen, ligand, receptor, oligonucleotide, hapten, epitope, mimitope, or an aptamer, and in a particular example, the second detection reagent is an antibody. More particularly, the capture reagent and the first and second detection reagents are antibodies to the analyte.

In embodiment (5), the anchoring oligonucleotide sequence can include a single stranded oligonucleotide sequence or a double stranded oligonucleotide sequence. In this embodiment, the extended sequence further can include one or more detection sequences and the measuring step further can include contacting the extended sequence with a plurality of labeled probes complementary to the one or more detection sequences. The extended sequence can also include one or more modified bases and the measuring step further can include contacting the extended sequence with a plurality of detectable moieties capable of binding to the one or more modified bases. The extended sequence can further comprise one or more labeled bases and the measuring step further can include detecting the presence of the one or more labeled bases. The one or more modified bases can comprise an aptamer, aptamer ligand, antibody, antigen, ligand, receptor, hapten, epitope, or a mimetope and the plurality of detectable moieties each comprise a binding partner of the one or more modified bases and a detectable label. For example, the one or more modified bases comprise streptavidin and the plurality of detectable moieties each comprise biotin and a detectable label; the one or more modified bases comprise biotin and the plurality of detectable moieties each comprise streptavidin and a detectable label; the one or more modified bases comprise avidin and the plurality of detectable moieties each comprise biotin and a detectable label;

and/or the one or more modified bases comprise biotin and the plurality of detectable moieties each comprise avidin and a detectable label.

Step (a) of embodiment (5) can include binding the analyte to the following species in the following order: (i) the capture reagent on a surface; and (ii) the detection reagent for the analyte. Alternatively, step (a) can include binding the analyte to the following species in the following order: (i) the detection reagent for the analyte; and (ii) the capture reagent on the surface; or step (a) can include binding the analyte to the following species simultaneously or substantially simultaneously: (i) the capture reagent on a surface; and (ii) the detection reagent for the analyte.

The extending step of embodiment (5) can include binding the probe to a template nucleic acid sequence and extending the probe by polymerase chain reaction. The extending step can further include binding the probe to a template nucleic acid sequence, forming a circular nucleic acid template, and extending the circular template by rolling circle amplification. The extended probe can remain localized on the surface following probe extension, e.g., the complex remains bound to the surface after the extending step. The extended probe can be bound to the anchoring reagent at a position within 10-100 μm of the location of the complex on the surface. The extending step can include PCR (Polymerase Chain Reaction), LCR (Ligase Chain Reaction), SDA (Strand Displacement Amplification), 3SR (Self-Sustained Synthetic Reaction), or isothermal amplification methods. In a particular example, the extending step can include isothermal amplification methods, e.g., is helicase-dependent amplification or rolling circle amplification (RCA).

The extension process of embodiment (5) can include contacting the complex formed in step (a) with a connector sequence comprising (i) an interior sequence complementary to the second probe and (ii) two end sequences complementary to non-overlapping regions of the first probe. The method can further include ligating the two end sequences of the connector oligonucleotide to form a circular target sequence that is hybridized to both the first and second probes. Alternatively, the extension process can include contacting the complex formed in step (a) of embodiment (5) with a first connector oligonucleotide sequence including a first connector probe sequence complementary to a first region of the first probe and a first region on the second probe, and a second connector oligonucleotide comprising a second probe sequence complementary to a second non-overlapping region of the first probe and a second non-overlapping region of the second probe; and optionally, ligating the first and second connector oligonucleotides to form a circular target sequence that is hybridized to both the first and second probes.

The surface of embodiment (5) can include a particle and/or an assay domain of an assay module such as a well of a multi-well plate or an assay chamber of a cartridge. The surface can include a plurality of distinct binding domains and the capture reagent and the anchoring reagent are located on two distinct binding domains on the surface. If the surface is a well of a plate, the well can include a plurality of distinct binding domains and the capture reagent and the anchoring reagent are located on two distinct binding domains within the well. The surface can also include a plurality of distinct binding domains and the capture reagent and the anchoring reagent are located on the same binding domain on the surface. If the surface is a well of a plate, the well can include a plurality of distinct binding domains and the capture reagent and the anchoring reagent are located on the same binding domain within the well. The capture reagent and the anchoring reagent can be within 10-100 nm on the surface. In a specific example, the surface can include an electrode and the measuring step further can include applying a voltage waveform to the electrode to generate an electrochemiluminesce signal, and optionally, the method of embodiment (5) further includes collecting the particle on an electrode and applying a voltage waveform to the electrode to generate an electrochemiluminescence signal.

The measuring step of embodiment (5) further can include binding the extended sequence to a detection probe having a detectable label, measuring the detectable label and correlating the measurement to the amount of analyte in the sample, wherein the detection probe comprising a nucleic acid sequence that is complementary to a region of the extended sequence. The detectable label can be measured by a measurement of light scattering, optical absorbance, fluorescence, chemiluminescence, electrochemiluminescence, bioluminescence, phosphorescence, radioactivity, magnetic field, or combinations thereof. In a particular example, the detectable label is an ECL label and the measuring step can include measuring an ECL signal.

Embodiment (6): a kit for the detection of an analyte of interest in a sample comprising, in one or more vials, containers, or compartments: (a) a surface comprising (i) a capture reagent for the analyte, and (ii) an anchoring reagent comprising an anchoring oligonucleotide sequence; (b) a first detection reagent for the analyte that is linked to a first nucleic acid probe; and (c) a second detection reagent for the analyte that is linked to a second nucleic acid probe.

The capture reagent of embodiment (6) can include an antibody, antigen, ligand, receptor, oligonucleotide, hapten, epitope, mimitope, or aptamer, and in a specific example the capture reagent can include an antibody. Likewise, the first detection reagent can include an antibody, antigen, ligand, receptor, oligonucleotide, hapten, epitope, mimitope, or aptamer, and in a specific example, the first detection reagent can include an antibody. Similarly, the second detection reagent can include an antibody, antigen, ligand, receptor, oligonucleotide, hapten, epitope, mimitope, or aptamer, and in a specific example, the second detection reagent can include an antibody.

The surface of embodiment (6) can comprise a particle and/or an assay domain of an assay module such as a well of a multi-well plate or an assay chamber of a cartridge. The surface can include a plurality of distinct binding domains and the capture reagent and the anchoring reagent are located on two distinct binding domains on the surface. If the surface is a well, the well can comprise a plurality of distinct binding domains and the capture reagent and the anchoring reagent are located on two distinct binding domains within the well. The surface can include a plurality of distinct binding domains and the capture reagent and the anchoring reagent are located on the same binding domain on the surface; and/or if the surface is a well, the well can include a plurality of distinct binding domains and the capture reagent and the anchoring reagent are located on the same binding domain within the well. The capture reagent and the anchoring reagent can be within 10-100 nm on the surface. In a specific example, the surface can include an electrode.

Embodiment (7): a method of detecting an analyte of interest in a sample comprising: (a) binding the analyte to: (i) a capture reagent for the analyte on a surface comprising the capture reagent and an anchoring reagent; (ii) a first detection reagent for the analyte comprising a first proximity probe, and (iii) a second detection reagent for the analyte comprising a second proximity probe; thereby forming a detection complex on the surface comprising the capture reagent, the analyte and the first and second detection reagents; (b) contacting the detection complex formed in (c) with a connector sequence comprising (i) an interior sequence complementary to the second proximity probe and (ii) two end sequences complementary to non-overlapping regions of the first proximity probe; (c) hybridizing the connector sequence to the first and second proximity probes; (d) ligating the two end sequences of the connector oligonucleotide to form a circular target sequence that is hybridized to both the first and second proximity probes; (e) extending the second proximity probe by rolling circle amplification of the target sequence to generate an amplicon comprising a binding domain that binds the anchoring reagent; (f) binding the amplicon to the anchoring reagent; and (g) measuring the amount of amplicon on the surface.

Embodiment (8): a method of detecting an analyte of interest in a sample comprising: (a) binding the analyte to: (i) a capture reagent for the analyte on a surface comprising the capture reagent and an anchoring reagent; (ii) a first detection reagent for the analyte comprising a first proximity probe, and (iii) a second detection reagent for the analyte comprising a second proximity probe; thereby forming a detection complex on the surface comprising the capture reagent, the analyte and the first and second detection reagents; (b) contacting the detection complex formed in (c) with a first connector oligonucleotide and a second connector oligonucleotide, wherein (i) a first end of the first connector and a first end of the second connector are complementary to two non-overlapping regions of the first proximity probe and (ii) a second end of the first connector and a second end of the second connector are complementary to two non-overlapping regions of the first proximity probe; (c) hybridizing the first and second connector oligonucleotides to the first and second proximity probes; (d) ligating the first and second connector oligonucleotides to form a circular target sequence that is hybridized to both the first and second proximity probes; (e) extending the second proximity probe by rolling circle amplification of the target sequence to generate an amplicon comprising a binding domain that binds the anchoring reagent; (f) binding the amplicon to the anchoring reagent; and (g) measuring the amount of amplicon on the surface.

The capture reagent of embodiments (7) and (8) can be an antibody, antigen, ligand, receptor, oligonucleotide, hapten, epitope, mimitope, or an aptamer, and in a specific example, the capture reagent is an antibody. Similarly, the first detection reagent can be an antibody, antigen, ligand, receptor, oligonucleotide, hapten, epitope, mimitope, or an aptamer, e.g., the first detection reagent is an antibody. In addition, the second detection reagent is an antibody, antigen, ligand, receptor, oligonucleotide, hapten, epitope, mimitope, or an aptamer, e.g., the second detection reagent is an antibody. In a specific example of embodiments (7) and (8), the capture reagent and the first and second detection reagents are antibodies to the analyte.

The anchoring reagent of embodiments (7) and (8) can include an oligonucleotide sequence, aptamer, aptamer ligand, antibody, antigen, ligand, receptor, hapten, epitope, or a mimetope. In one example, the binding domain can include an aptamer and the anchoring reagent can include an aptamer ligand. The binding domain can include a nucleic acid sequence and the anchoring reagent can include a DNA-binding protein; and/or the anchoring reagent can include an oligonucleotide sequence and the amplicon can include a complementary oligonucleotide sequence.

The amplicon of embodiments (7) and (8) can further comprise one or more detection sequences and the measuring step can further comprise contacting the extended sequence with a plurality of labeled probes complementary to the one or more detection sequences. Moreover, the amplicon may further comprise one or more modified bases and the measuring step further can include contacting the extended sequence with a plurality of detectable moieties capable of binding to the one or more modified bases. Still further, the amplicon may further include one or more labeled bases and the measuring step further can include detecting the presence of the one or more labeled bases. The one or more modified bases can comprise an aptamer, aptamer ligand, antibody, antigen, ligand, receptor, hapten, epitope, or a mimetope and the plurality of detectable moieties each comprise a binding partner of the one or more modified bases and a detectable label. The one or more modified bases can comprise streptavidin and the plurality of detectable moieties each comprise biotin and a detectable label; the one or more modified bases can comprise biotin and the plurality of detectable moieties each comprise streptavidin and a detectable label; the one or more modified bases can comprise avidin and the plurality of detectable moieties each comprise biotin and a detectable label; and/or the one or more modified bases can comprise biotin and the plurality of detectable moieties each comprise avidin and a detectable label.

Step (a) of embodiments (7) and (8) can comprise binding the analyte to the following species in the following order: (i) the capture reagent on a surface; and (ii) the first and second detection reagents for the analyte. Alternatively, step (a) can include binding the analyte to the following species in the following order: (i) the first and second detection reagents for the analyte; and (ii) the capture reagent on the surface. Still further, step (a) can include binding the analyte to the following species simultaneously or substantially simultaneously: (i) the capture reagent on a surface; and (ii) the first and second detection reagents for the analyte.

The amplicon of embodiments (7) and (8) can remain localized on the surface following probe extension. The complex can remain bound to the surface after the extending step. For example, the amplicon is bound to the anchoring reagent at a position within 10-100 μm of the location of the complex on the surface.

The surface of embodiments (7) and (8) can include a particle and/or an assay domain of an assay module such as a well of a multi-well plate or an assay chamber of a cartridge. The surface can include a plurality of distinct binding domains and the capture reagent and the anchoring reagent are located on two distinct binding domains on the surface. If the surface is a well of a plate, the well can comprise a plurality of distinct binding domains and the capture reagent and the anchoring reagent are located on two distinct binding domains within the well. The surface can include a plurality of distinct binding domains and the capture reagent and the anchoring reagent are located on the same binding domain on the surface. If the surface is a well of a plate, the well can include a plurality of distinct binding domains and the capture reagent and the anchoring reagent are located on the same binding domain within the well. In a specific example, the capture reagent and the anchoring reagent are within 10-100 nm on the surface.

Still further, the surface can include an electrode and the measuring step can include applying a voltage waveform to the electrode to generate an electrochemiluminesce signal. In these embodiments ((7) and (8)), the method can further include collecting the particle on an electrode and applying a voltage waveform to the electrode to generate an electrochemiluminescence signal. The measuring step can include binding the amplicon to a detection probe having a detectable label, measuring the detectable label and correlating the measurement to the amount of analyte in the sample, wherein the detection probe comprising a nucleic acid sequence that is complementary to a region of the amplicon. The detectable label is measured by a measurement of light scattering, optical absorbance, fluorescence, chemiluminescence, electrochemiluminescence, bioluminescence, phosphorescence, radioactivity, magnetic field, or combinations thereof. For example, the detectable label is an ECL label and the measuring step can include measuring an ECL signal.

Embodiment (9): a kit for the detection of an analyte of interest in a sample comprising, in one or more vials, containers, or compartments: (a) a surface comprising (i) a capture reagent for the analyte, and (ii) an anchoring reagent; (b) a first detection reagent for the analyte comprising a first proximity probe; (c) a second detection reagent for the analyte comprising a second proximity probe; and (d) a connector sequence comprising (i) an interior sequence complementary to the second proximity probe and (ii) two end sequences complementary to non-overlapping regions of the first proximity probe.

Embodiment (10): a kit for the detection of an analyte of interest in a sample comprising, in one or more vials, containers, or compartments: (a) a surface comprising (i) a capture reagent for the analyte, and (ii) an anchoring reagent; and (b) a first detection reagent for the analyte comprising a first proximity probe; (c) a second detection reagent for the analyte comprising a second proximity probe; and (d) (i) a first connector oligonucleotide and (ii) a second connector oligonucleotide, wherein (x) a first end of the first connector and a first end of the second connector are complementary to two non-overlapping regions of the first proximity probe and (y) a second end of the first connector and a second end of the second connector are complementary to two non-overlapping regions of the first proximity probe.

The capture reagent of embodiments (9) and (10) can include an antibody, antigen, ligand, receptor, oligonucleotide, hapten, epitope, mimitope, or aptamer. In a specific example, the capture reagent can include an antibody. The first detection reagent can include an antibody, antigen, ligand, receptor, oligonucleotide, hapten, epitope, mimitope, or aptamer, and in a specific example, the first detection reagent can include an antibody. The second detection reagent can include an antibody, antigen, ligand, receptor, oligonucleotide, hapten, epitope, mimitope, or aptamer, and in a specific example, the second detection reagent can include an antibody.

The surface of embodiments (9) and (10) can include a particle and/or an assay domain of an assay module such as a well of a multi-well plate or an assay chamber of a cartridge. The surface can include a plurality of distinct binding domains and the capture reagent and the anchoring reagent are located on two distinct binding domains on the surface. If the surface is a well of a plate, the well can include a plurality of distinct binding domains and the capture reagent and the anchoring reagent are located on two distinct binding domains within the well. The surface can include a plurality of distinct binding domains and the capture reagent and the anchoring reagent are located on the same binding domain on the surface. If the surface is a well, the well can include a plurality of distinct binding domains and the capture reagent and the anchoring reagent are located on the same binding domain within the well. In a specific example, the capture reagent and the anchoring reagent are within 10-100 nm on the surface.

The surface of embodiments (9) and (10) can include an electrode.

Embodiment (11): a method of detecting an analyte of interest in a sample comprising: (a) binding the analyte to: (i) a capture reagent for the analyte on a surface comprising the capture reagent and an anchoring reagent comprising an anchoring oligonucleotide sequence; (ii) a first detection reagent for the analyte comprising a first proximity probe, and (iii) a second detection reagent for the analyte comprising a second proximity probe; thereby forming a detection complex on the surface comprising the capture reagent, the analyte and the first and second detection reagents; (b) contacting the detection complex formed in (c) with a connector sequence comprising (i) an interior sequence complementary to the second proximity probe, (ii) two end sequences complementary to non-overlapping regions of the first proximity probe and (iii) a sequence matching the anchoring sequence; (c) hybridizing the connector sequence to the first and second proximity probes; (d) ligating the two end sequences of the connector oligonucleotide to form a circular target sequence that is hybridized to both the first and second proximity probes; (e) extending the second proximity probe by rolling circle amplification of the target sequence to generate an amplicon comprising a plurality of anchoring sequence complements that are complementary to the anchoring sequence; (f) hybridizing the anchoring sequence to one of the anchoring sequence complements; and (g) measuring the amount of amplicon on the surface.

Embodiment (12): a method of detecting an analyte of interest in a sample comprising: (a) binding the analyte to: (i) a capture reagent for the analyte on a surface comprising the capture reagent and an anchoring reagent comprising an anchoring oligonucleotide sequence; (ii) a first detection reagent for the analyte comprising a first proximity probe, and (iii) a second detection reagent for the analyte comprising a second proximity probe; thereby forming a detection complex on the surface comprising the capture reagent, the analyte and the first and second detection reagents; (b) contacting the detection complex formed in (a) with a first connector oligonucleotide and a second connector oligonucleotide, wherein (i) a first end of the first connector and a first end of the second connector are complementary to two non-overlapping regions of the first proximity probe, (ii) a second end of the first connector and a second end of the second connector are complementary to two non-overlapping regions of the first proximity probe and (iii) the first and/or second connector also comprise a sequence matching the anchoring sequence; (c) hybridizing the first and second connector oligonucleotides to the first and second proximity probes; (d) ligating the first and second connector oligonucleotides to form a circular target sequence that is hybridized to both the first and second proximity probes; (e) extending the second proximity probe by rolling circle amplification of the target sequence to generate an amplicon comprising a plurality of anchoring sequence complements that are complementary to the anchoring sequence; (f) hybridizing the anchoring sequence to one of the anchoring sequence complements; and (g) measuring the amount of amplicon on the surface.

The capture reagent of embodiments (11) and (12) is an antibody, antigen, ligand, receptor, oligonucleotide, hapten, epitope, mimitope, or an aptamer. In a specific example, the capture reagent is an antibody. The first detection reagent is an antibody, antigen, ligand, receptor, oligonucleotide, hapten, epitope, mimitope, or an aptamer, and in a specific example, the first detection reagent is an antibody. Likewise, the second detection reagent is an antibody, antigen, ligand, receptor, oligonucleotide, hapten, epitope, mimitope, or an aptamer, and in a specific example, the second detection reagent is an antibody. In one example, the first and second detection reagents are antibodies to the analyte.

The amplicon of embodiments (11) and (12) can further comprise one or more detection sequences and the measuring step can include contacting the extended sequence with a plurality of labeled probes complementary to the one or more detection sequences. Moreover, the amplicon can also comprise one or more modified bases and the measuring step can include contacting the extended sequence with a plurality of detectable moieties capable of binding to the one or more modified bases. The amplicon additionally include one or more labeled bases and the measuring step can include detecting the presence of the one or more labeled bases. The one or more modified bases comprise an aptamer, aptamer ligand, antibody, antigen, ligand, receptor, hapten, epitope, or a mimetope and the plurality of detectable moieties each comprise a binding partner of the one or more modified bases and a detectable label. The one or more modified bases can comprise streptavidin and the plurality of detectable moieties each comprise biotin and a detectable label; the one or more modified bases can comprise biotin and the plurality of detectable moieties each comprise streptavidin and a detectable label; the one or more modified bases can comprise avidin and the plurality of detectable moieties each comprise biotin and a detectable label; and/or the one or more modified bases can include biotin and the plurality of detectable moieties each comprise avidin and a detectable label.

Step (a) of embodiments (11) and (12) can comprise binding the analyte to the following species in the following order: (i) the capture reagent on a surface; and (ii) the first and second detection reagents for the analyte. Alternatively, step (a) can include binding the analyte to the following species in the following order: (i) the first and second detection reagents for the analyte; and (ii) the capture reagent on the surface. Still further, step (a) can include binding the analyte to the following species simultaneously or substantially simultaneously: (i) the capture reagent on a surface; and (ii) the first and second detection reagents for the analyte.

The amplicon in embodiments (11) and (12) can remain localized on the surface following probe extension, and optionally, the complex remains bound to the surface after the extending step. For example, the amplicon is bound to the anchoring reagent at a position within 10-100 μm of the location of the complex on the surface.

The surface of embodiments (11) and (12) can include a particle and/or an assay domain of an assay module such as a well of a multi-well plate or an assay chamber of a cartridge. Optionally, the surface can include a plurality of distinct binding domains and the capture reagent and the anchoring reagent are located on two distinct binding domains on the surface. If the surface is a well, the well can include a plurality of distinct binding domains and the capture reagent and the anchoring reagent are located on two distinct binding domains within the well. The surface can include a plurality of distinct binding domains and the capture reagent and the anchoring reagent are located on the same binding domain on the surface. If the surface is a well, the well can comprise a plurality of distinct binding domains and the capture reagent and the anchoring reagent are located on the same binding domain within the well. The capture reagent and the anchoring reagent can be within 10-100 nm on the surface.

The surface of embodiments (11) and (12) can comprise an electrode and the measuring step can include applying a voltage waveform to the electrode to generate an electrochemiluminesce signal. Optionally, embodiments (11) and (12) further comprise collecting the particle on an electrode and applying a voltage waveform to the electrode to generate an electrochemiluminescence signal. The measuring step can also include binding the amplicon to a detection probe having a detectable label, measuring the detectable label and correlating the measurement to the amount of analyte in the sample, wherein the detection probe comprising a nucleic acid sequence that is complementary to a region of the amplicon. The detectable label can be measured by a measurement of light scattering, optical absorbance, fluorescence, chemiluminescence, electrochemiluminescence, bioluminescence, phosphorescence, radioactivity, magnetic field, or combinations thereof. In one example, the detectable label is an ECL label and the measuring step can include measuring an ECL signal.

The sample of embodiments (11) and (12) can comprise one or more analyte molecules, and the surface can include a plurality of capture reagents for the one or more analyte molecules distributed across a plurality of resolvable binding regions positioned on the surface, and the method can include: (x) binding the one or more analyte molecules to one or more capture reagents on the surface; (y) determining the presence or absence of an analyte molecule in each binding region; and (z) identifying the number of binding regions that contain an analyte molecule and/or the number of analyte domains that do not contain an analyte molecule. The measuring step can include imaging an optical signal from the surface to generate an image comprising a plurality of pixels and each resolvable binding region maps to one or more pixels in the image. The resolvable binding regions can be elements of an array and/or the resolvable binding regions are configured to isolate individual particles. Each resolvable binding region can be an individual nano-wells having a volume <100 nL, e.g., wherein at least 99% of the binding regions contain either zero or one analyte molecule, wherein at least about 95% of the binding regions contain either zero or one analyte molecule, wherein at least about 80% of the binding regions contain either zero or one analyte molecule, and/or wherein at least about 50% of the binding regions contain either zero or one analyte molecule. The concentration of analyte molecules in the sample in embodiments (11) and (12) can be determined at least in part using a calibration curve, a Poisson distribution analysis and/or a Gaussian distribution analysis of the number of binding regions that contain at least one or one analyte molecule.

In embodiments (11) and (12), the sample can comprise one or more analyte molecules, the surface can include a plurality of particles each comprising a plurality of binding reagents for an analyte molecule wherein the plurality of particles is distributed across a plurality of resolvable binding regions, and the method can include: (i) binding the one or more analyte molecules to one or more binding reagents on the surface, and (ii) distributing the plurality of particles across an array of resolvable binding regions; and (iii) determining the presence or absence of an analyte molecule in each resolvable binding regions, so as to identify the number of binding regions that contain an analyte molecule and/or the number of binding regions that do not contain an analyte molecule.

Embodiment (13): a kit for the detection of an analyte of interest in a sample comprising, in one or more vials, containers, or compartments: (a) a surface comprising (i) a capture reagent for the analyte, and (ii) an anchoring reagent comprising an anchoring oligonucleotide sequence; (b) a first detection reagent for the analyte comprising a first proximity probe; (c) a second detection reagent for the analyte comprising a second proximity probe; and (d) a connector sequence comprising (i) an interior sequence complementary to the second proximity probe and (ii) two end sequences complementary to non-overlapping regions of the first proximity probe.

Embodiment (14): a kit for the detection of an analyte of interest in a sample comprising, in one or more vials, containers, or compartments: (a) a surface comprising (i) a capture reagent for the analyte, and (ii) an anchoring reagent comprising an anchoring oligonucleotide sequence; and (b) a first detection reagent for the analyte comprising a first proximity probe; (c) a second detection reagent for the analyte comprising a second proximity probe; and (d) (i) a first connector oligonucleotide and (ii) a second connector oligonucleotide, wherein (x) a first end of the first connector and a first end of the second connector are complementary to two non-overlapping regions of the first proximity probe and (y) a second end of the first connector and a second end of the second connector are complementary to two non-overlapping regions of the first proximity probe.

The capture reagent of embodiments (13) and (14) can comprise an antibody, antigen, ligand, receptor, oligonucleotide, hapten, epitope, mimitope, or aptamer, e.g., the capture reagent can include an antibody. Likewise, the first detection reagent can include an antibody, antigen, ligand, receptor, oligonucleotide, hapten, epitope, mimitope, or aptamer, e.g., the first detection reagent can include an antibody. Similarly, the second detection reagent can include an antibody, antigen, ligand, receptor, oligonucleotide, hapten, epitope, mimitope, or aptamer, e.g., the second detection reagent can include an antibody.

The surface of embodiments (13) and (14) can include a particle and/or an assay domain of an assay module such as a well of a multi-well plate or an assay chamber of a cartridge. The can include a plurality of distinct binding domains and the capture reagent and the anchoring reagent are located on two distinct binding domains on the surface. If the surface is a well, the well can comprise a plurality of distinct binding domains and the capture reagent and the anchoring reagent are located on two distinct binding domains within the well. The surface can include a plurality of distinct binding domains and the capture reagent and the anchoring reagent are located on the same binding domain on the surface. If the surface is a well, the well can include a plurality of distinct binding domains and the capture reagent and the anchoring reagent are located on the same binding domain within the well. The capture reagent and the anchoring reagent can be within 10-100 nm on the surface, and optionally, the surface can include an electrode.

Embodiment (15): a method of detecting analytes in a sample, wherein the method can include: (a) binding the analytes to first and second detection reagents to form detection complexes, each detection complex comprising an analyte, a first detection reagent and a second detection reagent, wherein the first detection reagent has a first detectable label and the second detection reagent has a second detectable label, (b) partitioning the analytes across a plurality of reaction vessels so that the majority of reaction vessels contain one or fewer analytes; and (c) detecting the number of analyte molecules by counting the number of reaction vessels that contain the first and second detectable labels. In this embodiment (15), the first detection reagent can be an antibody, antigen, ligand, receptor, oligonucleotide, hapten, epitope, mimitope, or an aptamer, e.g., the first detection reagent is an antibody. Likewise, the second detection reagent can be an antibody, antigen, ligand, receptor, oligonucleotide, hapten, epitope, mimitope, or an aptamer, e.g., the second detection reagent is an antibody. In a specific example, the first and second detection reagents are antibodies to the analyte.

Step (a) of embodiment (15) can further comprise forming a solution comprising said analytes and said detection reagents and step (b) can include partitioning the solution across the plurality of reaction vessels so that the likelihood of finding an unbound first detection reagent and an unbound second detection reagent in the same vessel is less than 1 in 10. Alternatively, step (a) of embodiment (15) can further comprise forming a solution comprising said analytes and said detection reagents and step (b) can include partitioning the solution across the plurality of reaction vessels so that the likelihood of finding an unbound first detection reagent and an unbound second detection reagent in the same vessel is less than 1 in 100. Still further, step (a) of embodiment (15) can further comprise forming a solution comprising said analytes and said detection reagents and step (b) can include partitioning the solution across the plurality of reaction vessels so that the likelihood of finding an unbound first detection reagent and an unbound second detection reagent in the same vessel is less than 1 in 1000. Moreover, step (a) of embodiment (15) can further comprise forming a solution comprising said analytes and said detection reagents and step (b) can include partitioning the solution across the plurality of reaction vessels so that the likelihood of finding an unbound first detection reagent and an unbound second detection reagent in the same vessel is less than 1 in 10000.

Embodiment (16): a method of detecting analytes in a sample, the method comprising: (a) binding the analytes to capture reagents and first and second detection reagents to form detection complexes, each detection complex comprising a capture reagent, an analyte, a first detection reagent and a second detection reagent, wherein (i) the first detection reagent has a first detectable label and the second detection reagent has a second detectable label, (ii) the capture reagent is on a surface; (b) partitioning the analytes across a plurality of reaction vessels so that the majority of reaction vessels contain one or fewer analytes; and (c) detecting the number of analyte molecules by counting the number of reaction vessels that contain the first and second detectable labels. In this embodiment, the capture reagent can be an antibody, antigen, ligand, receptor, oligonucleotide, hapten, epitope, mimitope, or an aptamer, e.g., the capture reagent is an antibody. Likewise, the first detection reagent can be an antibody, antigen, ligand, receptor, oligonucleotide, hapten, epitope, mimitope, or an aptamer, e.g., the first detection reagent is an antibody. Moreover, the second detection reagent can be an antibody, antigen, ligand, receptor, oligonucleotide, hapten, epitope, mimitope, or an aptamer, e.g., the second detection reagent is an antibody. For example, the capture reagent, first and second detection reagents are antibodies to the analyte.

Step (b) of embodiment (16) can further comprise partitioning the solution across the plurality of reaction vessels so that the likelihood of finding an unbound first detection reagent and an unbound second detection reagent in the same vessel is less than 1 in 10. Moreover, step (b) of embodiment (16) can further comprise partitioning the solution across the plurality of reaction vessels so that the likelihood of finding an unbound first detection reagent and an unbound second detection reagent in the same vessel is less than 1 in 100. Step (b) of embodiment (16) can further comprise partitioning the solution across the plurality of reaction vessels so that the likelihood of finding an unbound first detection reagent and an unbound second detection reagent in the same vessel is less than 1 in 1000. Further, step (b) of embodiment (16) can further comprise partitioning the solution across the plurality of reaction vessels so that the likelihood of finding an unbound first detection reagent and an unbound second detection reagent in the same vessel is less than 1 in 10000.

The capture reagent in the detection complex of embodiment (16) can be on the surface prior to binding the capture reagent to the analyte; or the capture reagent in the detection complex binds to the analyte prior to immobilizing the capture reagent on the surface. In one example, the capture reagent can include a targeting moiety and the surface can include a targeting moiety complement. The targeting moiety and the targeting agent binding partner are selected from the following binding pairs: avidin-biotin, streptavidin-biotin, receptor-ligand, antibody-antigen, nucleic acid-nucleic acid complement.

The surface of embodiment (16) is a particle, and optionally, the capture reagents are immobilized on a plurality of particles and the partitioning of analytes is achieved by binding the analytes to the capture reagents and partitioning the particles into the plurality of reaction vessels. The capture reagents can be immobilized on a plurality of particles and the partitioning of analytes is achieved by partitioning the particles into a plurality of reaction vessels and then binding the analytes to the capture reagents.

Embodiment (16) can further comprise partitioning a plurality of particles into the plurality of reaction vessels, wherein the plurality of particles comprise targeting moieties, the capture reagents comprise a targeting moiety complement and the partitioning of analytes is achieved by binding the targeting moiety complements to the targeting moieties. Embodiment (16) can also include washing the particles prior to the partitioning step and/or after the partitioning step.

The surface of embodiment (16) can be a location within one of the reaction vessels. In this embodiment, the capture reagents can be immobilized on surfaces of the plurality of reaction vessels and the partitioning of analytes is achieved by binding the analytes to the capture reagents. Optionally, the reaction vessels have surfaces with targeting moieties immobilized thereon, the capture reagents comprise targeting moiety complements, and the partitioning of analytes is achieved by binding the targeting moiety complements to the targeting moieties. In this specific example, the method can further comprise washing the reaction vessel prior to the detection step.

The plurality of reaction vessels of embodiment (16) can comprise an array of nanowells. The plurality of reaction vessels can comprise at least 10,000 reaction vessels. In one embodiment, the reaction vessels have a volume of less than 100 nL. Optionally, less than 50% of the reaction vessels contain an analyte at the time of detection, less than 10% of the reaction vessels contain an analyte at the time of detection, less than 1% of the reaction vessels contain an analyte at the time of detection, and/or less than 0.1% of the reaction vessels contain an analyte at the time of detection.

In one aspect of embodiment (16), the first detectable label is a first enzyme of a coupled enzyme reaction system and the second detectable label is a second enzyme of the couple enzyme reaction system and the step (d) can include adding one or more substrates of the reaction system, producing a product of the enzyme reaction system and counting the reaction vessels that contain the product. In this embodiment, the product may only be produced when the first enzyme and second enzyme are in close proximity, e.g., the first and second enzymes are within 200 nM of each other, or the first and second enzymes are within 50 nM of each other. For example, the first enzyme is an oxidase, the second enzyme is a peroxidase, and the substrates comprise an oxidase substrate and a labeled Amplex Red or luminol derivative. In this embodiment, the oxidase can be glucose oxidase and the oxidase substrate is glucose. In one embodiment, the reactions catalyzed by the first and second enzymes in the detection complex lead to immobilization of the labeled Amplex Red or luminol on the surface, and optionally, the method can include measuring the labeled Amplex Red or luminol on the surface. The labeled Amplex Red or luminol is optionally biotin-Amplex Red or luminol, and the method can include adding labeled streptavidin and measuring the labels on the streptavidin.

Step (d) of embodiment (16) may include measuring a proximity-dependent signal that is generated when the first and second detectable labels are bound to the same analyte molecule and counting the number of reaction vessels that produce the proximity-dependent signal, e.g., the proximity-dependent signal is generated by PLA-RCA. For example, the first detectable label can be a FRET donor and the detectable label is a FRET acceptor and the proximity-dependent signal is measured by exciting the FRET donor and measuring emission from the FRET acceptor. In one example, the first and second detectable labels can be measured independently. Optionally, the first and second detectable labels are luminescent labels that differ from one another with respect to spectral properties. In one example, the first detectable label is a first enzyme that reacts with a first substrate to produce a first signal and the second detectable label is a second enzyme that reacts with a second substrate to produce a different second signal, and step (d) of embodiment (16) can include adding the first enzyme substrate and the second enzyme substrate and counting the number of reaction vessels in which the first and second signals are generated. The first and second signals can be changes in optical absorbance with different spectral properties. Optionally, first and second signals are luminescent signals with different spectral properties. The first and second enzymes can be hydrolytic enzymes, e.g., selected from a phosphatase, sulfatase, galactosidase, glucuronidase, or combinations thereof, and the first and second substrates are selected from phosphate, sulfate, galactoside and glucuronide modified stabilized dioxetanes, 4-methylumbelliferyl, fluorescein, or combinations thereof. In a specific example, the first and second enzymes are selected from horseradish peroxidase, beta-galactosidase, and alkaline phosphatase. The detection step of embodiment (16) can include detection via light scattering, optical absorbance, fluorescence, chemiluminescence, electrochemiluminescence, luminescence, radioactivity, magnetic field, or combinations thereof.

Embodiment (17): a kit for the detection of analytes in a sample, the kit comprising, in one or more vials, containers, or compartments: (a) a first detection reagent comprising a first detectable label; (b) a second detection reagent comprising a second detectable label; (c) a plurality of reaction vessels configured to contain one or fewer analyte molecules.

Embodiment (18): a kit for the detection of analytes in a sample, the kit comprising, in one or more vials, containers, or compartments: (a) a first detection reagent comprising a first detectable label; (b) a second detection reagent comprising a second detectable label; (c) a surface comprising a capture reagent; and (d) a plurality of reaction vessels configured to contain one or fewer analyte molecules.

The first and second detection reagents of embodiments (17) and (18) can comprise an antibody, antigen, ligand, receptor, oligonucleotide, hapten, epitope, mimitope, aptamer, or combinations thereof. In one example, the first and second detection reagents comprise an antibody. The capture antibody can comprise an antibody, antigen, ligand, receptor, oligonucleotide, hapten, epitope, mimitope, or aptamer, e.g., the capture antibody can include an antibody. In one example, the capture reagent can include a targeting moiety and the surface can include a targeting moiety complement, e.g., the targeting moiety and the targeting agent binding partner are selected from the following binding pairs: avidin-biotin, streptavidin-biotin, receptor-ligand, antibody-antigen, nucleic acid-nucleic acid complement.

The surface of embodiments (17) and (18) can be a particle, and for example, the capture reagents are immobilized on a plurality of particles. Alternatively, the surface is a location within one of the reaction vessels and e.g., the capture reagents are immobilized on surfaces of the plurality of reaction vessels. Optionally, the reaction vessels have surfaces with targeting moieties immobilized thereon and the capture reagents comprise targeting moiety complements. The plurality of reaction vessels can comprise an array of nanowells or water droplets dispersed in a water-in-oil emulsion. The plurality of reaction vessels can include at least 10,000 reaction vessels and optionally, a reaction vessel in the plurality has a volume of less than 100 nL.

In the kit of embodiments (17) and (18), the first detectable label can be a first enzyme of a coupled enzyme reaction system and the second detectable label is a second enzyme of the couple enzyme reaction system and the kit can include, in one or more additional vials, containers, or compartments, one or more substrates of the reaction system. For example, the first enzyme is an oxidase, the second enzyme is a peroxidase, and the substrates comprise an oxidase substrate and a labeled Amplex Red or luminol derivative. In a specific embodiment, the oxidase is glucose oxidase and the oxidase substrate is glucose. The first and second detectable labels can be components of a proximity-dependent system, e.g., the first detectable label is a FRET donor and the detectable label is a FRET acceptor. The first and second detectable labels can be measured independently. Optionally, the first and second detectable labels are luminescent labels that differ from one another with respect to spectral properties.

In the kit of embodiments (17) and (18), the first detectable label is a first enzyme that reacts with a first substrate to produce a first signal and the second detectable label is a second enzyme that reacts with a second substrate to produce a different second signal, and the kit can include, in one or more vials, containers, or compartments, the first enzyme substrate and the second enzyme substrate. Optionally, the first and second signals are changes in optical absorbance with different spectral properties. In one example, the first and second signals are luminescent signals with different spectral properties. The first and second enzymes can be hydrolytic enzymes. In one example, the first and second enzymes are selected from a phosphatase, sulfatase, galactosidase, glucuronidase, or combinations thereof. The first and second substrates can be selected from phosphate, sulfate, galactoside and glucuronide modified stabilized dioxetanes, 4-methylumbelliferyl, fluorescein, or combinations thereof. Optionally, the first and second enzymes are selected from horseradish peroxidase, beta-galactosidase, and alkaline phosphatase.

Embodiment (19): a method of detecting an analyte of interest in a sample comprising: (a) binding the analyte to a capture reagent, a first detection reagent having a first detectable label and a second detection reagent having a second detectable label and forming a complex, wherein the capture reagent in the complex is immobilized on a surface; (b) cross-linking the first and second detection reagent to form a cross-linked product; (c) releasing the cross-linked product from the surface into an eluent; (d) counting individual cross-linked products in the eluent that comprise both the first and second detectable labels. In this example (19), the capture reagent is an antibody, antigen, ligand, receptor, oligonucleotide, hapten, epitope, mimitope, or an aptamer, and in a specific example, the capture reagent is an antibody. Likewise, the first detection reagent can be an antibody, antigen, ligand, receptor, oligonucleotide, hapten, epitope, mimitope, or an aptamer, and in a specific example, the first detection reagent is an antibody. Moreover, the second detection reagent is an antibody, antigen, ligand, receptor, oligonucleotide, hapten, epitope, mimitope, or an aptamer, and specifically, the second detection reagent can be an antibody. In one particular example, the capture reagent and the first and second detection reagents are antibodies to the analyte.

Embodiment (19) can further comprise adding a cross-linking agent to cross-link the first and second detection reagents, e.g., the first and second detection reagents comprise reactive moieties and the cross-linking agent is a multifunctional cross-linking agent that links to the reactive moieties. For example, the reactive moieties comprise an amine, thiol, hydrazide, aldehyde, ester, iodoacetamide, maleimide, click chemistry reagents, and combinations thereof. The cross-linking agents can comprise an amine, thiol, hydrazide, aldehyde, ester, iodoacetamide, maleimide, click chemistry reagents, and combinations thereof. The first and second detection reagents can include binding moieties and the cross-linking agent is a multivalent binding partner of the binding moieties. In one example, the first and second detection reagents are antibodies of an animal species and the cross-linking agent is a multivalent anti-species antibody targeting antibodies of the animal species. The first and second detection reagents can comprise biotin and the cross-linking agent is streptavidin; the first and second detection reagents include streptavidin and the cross-linking agent is biotin; the first and second detection reagents are linked to streptavidin and the cross-linking agent is a polymer comprising a plurality of biotin molecules; and/or the first and second detection reagents comprise first and second nucleic acid probes, respectively, and the cross-linking agent is an oligonucleotide that can include a sequence complementary to the first nucleic acid probe and a separate sequence complementary to the second nucleic acid probe.

The surface of embodiment (19) can comprise a particle, a reaction vessel, e.g., a tube or ampoule, and/or the surface can include an assay domain of an assay module such as a well of a multi-well plate or an assay chamber of a cartridge. The method of embodiment (19) can further include collecting the particles and washing the particles to remove impurities and optionally, the first and second detectable labels are measured by a measurement of light scattering, optical absorbance, fluorescence, chemiluminescence, electrochemiluminescence, bioluminescence, phosphorescence, radioactivity, magnetic field, or combinations thereof. In a specific example, the first and second detectable labels comprise an ECL label and the counting step can include measuring an ECL signal.

Embodiment (20): a kit for the detection of an analyte of interest in a sample comprising, in one or more vials, containers, or compartments: (a) a surface comprising an immobilized capture reagent; (b) a first detection reagent having a first detectable label; (c) a second detection reagent having a second detectable label; and (d) a cross-linking agent reactive with the first and second detection reagents.

The first and second detection reagents of embodiment (20) can comprise reactive moieties and the cross-linking agent is a multifunctional cross-linking agent that links to the reactive moieties. The reactive moieties can include an amine, thiol, hydrazide, aldehyde, ester, iodoacetamide, maleimide, click chemistry reagents, and combinations thereof; and the cross-linking agents can include an amine, thiol, hydrazide, aldehyde, ester, iodoacetamide, maleimide, click chemistry reagents, and combinations thereof. The first and second detection reagents of embodiment (20) can comprise binding moieties and the cross-linking agent is a multivalent binding partner of the binding moieties, e.g., the first and second detection reagents are antibodies of an animal species and the cross-linking agent is a multivalent anti-species antibody targeting antibodies of the animal species; the first and second detection reagents comprise biotin and the cross-linking agent is streptavidin; the first and second detection reagents comprise streptavidin and the cross-linking agent is biotin; the first and second detection reagents are linked to streptavidin and the cross-linking agent is a polymer comprising a plurality of biotin molecules; and/or the first and second detection reagents comprise first and second nucleic acid probes, respectively, and the cross-linking agent is an oligonucleotide that can include a sequence complementary to the first nucleic acid probe and a separate sequence complementary to the second nucleic acid probe.

The surface of embodiment (20) can include a particle, an assay domain of an assay module such as a well of a multi-well plate, or an assay chamber of a cartridge, or a reaction vessel, e.g., a tube or ampoule. In addition, the surface can include a plurality of distinct binding domains and the capture reagent is located on a distinct binding domain on the surface. If the surface is a well, the well can include a plurality of distinct binding domains and the capture reagent is located on a distinct binding domain within the well. The surface can also include an electrode.

Embodiment (21): a method of detecting an analyte of interest in a sample comprising: (a) binding the analyte to a capture reagent, a first detection reagent and a second detection reagent to form a complex, wherein the first detection reagent can include a first detectable label and a first nucleic acid probe, the second detection reagent can include a second detectable label and a second nucleic acid probe, and the capture reagent in the complex is immobilized on a surface; (b) cross-linking the first and second detection reagent by (i) hybridizing the first probe to the second probe, (ii) hybridizing the first and second probes to a third nucleic acid having regions complementary to the first and second probes, or (iii) ligating the first and second probes; (c) releasing the cross-linked product from the surface into an eluent; (d) counting individual cross-linked products in the eluent that comprise both the first and second detectable labels.

The capture reagent of embodiment (21) can be an antibody, antigen, ligand, receptor, oligonucleotide, hapten, epitope, mimitope, or an aptamer, e.g., the capture reagent is an antibody. Likewise, the first detection reagent is an antibody, antigen, ligand, receptor, oligonucleotide, hapten, epitope, mimitope, or an aptamer, e.g., the first detection reagent is an antibody; the second detection reagent can be an antibody, antigen, ligand, receptor, oligonucleotide, hapten, epitope, mimitope, or an aptamer, e.g., the second detection reagent is an antibody. In a specific example, the capture reagent and the first and second detection reagents are antibodies to the analyte.

The surface of embodiment (21) can include a particle, a reaction vessel, e.g., a tube or ampoule, or an assay domain of an assay module such as a well of a multi-well plate or an assay chamber of a cartridge. The method of embodiment (21) can further comprise collecting the particles and washing the particles to remove impurities. The first and second detectable labels can be measured by a measurement of light scattering, optical absorbance, fluorescence, chemiluminescence, electrochemiluminescence, bioluminescence, phosphorescence, radioactivity, magnetic field, or combinations thereof. In a specific example, the first and second detectable labels comprise an ECL label and the counting step can include measuring an ECL signal.

Embodiment (22): a kit for the detection of an analyte of interest in a sample comprising, in one or more vials, containers, or compartments: (a) a surface comprising an immobilized capture reagent; (b) a first detection reagent having a first detectable label and a first nucleic acid probe; (c) a second detection reagent having a second detectable label and a second nucleic acid probe; and (d) a third nucleic acid having regions complementary to the first and second nucleic acid probes.

The surface of embodiment (22) can include a particle, an assay domain of an assay module such as a well of a multi-well plate, or an assay chamber of a cartridge, or a reaction vessel, e.g., a tube or ampoule. The surface can include a plurality of distinct binding domains and the capture reagent is located on a distinct binding domain on the surface, and if the surface is a well, the well can comprise a plurality of distinct binding domains and the capture reagent is located on a distinct binding domain within the well. The surface optionally can include an electrode.

Embodiment (23): a method of detecting an analyte of interest in a sample comprising: (a) binding the analyte to a capture reagent, a first detection reagent and a second detection reagent to form a complex, wherein the first detection reagent can include a first nucleic acid probe, the second detection reagent can include a second nucleic acid probe, and the capture reagent in the complex is immobilized on a surface; (b) extending the second nucleic acid probe to form an extended sequence comprising a detectable label, the extension being dependent on the co-localization of the first and second nucleic acid probes in the complex; (c) releasing the extended sequence from the surface into an eluent; and (d) counting individual extended sequences in the eluent. In this embodiment, the capture reagent is an antibody, antigen, ligand, receptor, oligonucleotide, hapten, epitope, mimitope, or an aptamer. In a specific example, the capture reagent is an antibody. Likewise, the first detection reagent is an antibody, antigen, ligand, receptor, oligonucleotide, hapten, epitope, mimitope, or an aptamer, and in a specific example, the first detection reagent is an antibody. The second detection reagent is an antibody, antigen, ligand, receptor, oligonucleotide, hapten, epitope, mimitope, or an aptamer, and specifically, the second detection reagent is an antibody. In a specific example, the capture reagent and the first and second detection reagents are antibodies to the analyte.

The surface of embodiment (23) can include a particle, a reaction vessel, e.g., a tube or ampoule; or an assay domain of an assay module such as a well of a multi-well plate or an assay chamber of a cartridge. The method of embodiment (23) can further comprise collecting the particles and washing the particles to remove impurities.

The label of embodiment (23) can be measured by a measurement of light scattering, optical absorbance, fluorescence, chemiluminescence, electrochemiluminescence, bioluminescence, phosphorescence, radioactivity, magnetic field, or combinations thereof. In a specific example, the label can include an ECL label and the counting step can include measuring an ECL signal.

The extending step of embodiment (23) can include binding the probe to a template nucleic acid sequence and extending the probe by polymerase chain reaction. The extending step can also comprise binding the first probe to a template nucleic acid sequence, forming a circular nucleic acid template, and extending the circular template by rolling circle amplification. The extending step may comprise binding the first probe to a template nucleic acid sequence, binding the second probe to the template sequence, and ligating the first and second probes. Optionally, the label is a fluorescent label and the counting of individual extended sequences can include single molecule fluorescence detection, e.g., can include fluorescence correlation spectroscopy and/or fluorescence cross-correlation spectroscopy. Single molecule fluorescence detection can comprise flowing the eluent through a capillary, focusing a light source on a volume within the capillary to create an interrogation zone and observing the interrogation zone with a light detector to detect the passage of fluorescent molecules through the interrogation zone. Single molecule fluorescence detection can also comprise flowing the eluent through a capillary, focusing a light source on a volume within the capillary to create an interrogation zone and observing the interrogation zone with a light detector to detect the passage of fluorescent molecules through the interrogation zone.

Embodiment (24): method of detecting an analyte of interest in a sample comprising: (a) binding the analyte to a capture reagent, a first detection reagent having a first detectable label and a second detection reagent having a second detectable label and forming a complex, wherein the capture reagent in the complex is immobilized on a surface; (b) releasing the formed complex from the surface, by dissociating the immobilized capture reagent from surface into an eluent; and (c) counting individual products in the eluent that comprise both the first and second detectable labels. In this embodiment, the capture reagent is an antibody, antigen, ligand, receptor, oligonucleotide, hapten, epitope, mimitope, or an aptamer, e.g., the capture reagent is an antibody; the first detection reagent is an antibody, antigen, ligand, receptor, oligonucleotide, hapten, epitope, mimitope, or an aptamer, e.g., the first detection reagent is an antibody; the second detection reagent is an antibody, antigen, ligand, receptor, oligonucleotide, hapten, epitope, mimitope, or an aptamer, e.g., the second detection reagent is an antibody; and in a specific example, the capture reagent and the first and second detection reagents are antibodies to the analyte.

The surface of embodiment (24) can comprise a particle, a reaction vessel, e.g., a tube or ampoule, and/or an assay domain of an assay module such as a well of a multi-well plate or an assay chamber of a cartridge. The method of embodiment (24) can include collecting the particles and washing the particles to remove impurities. The first and second detectable labels can be measured by a measurement of light scattering, optical absorbance, fluorescence, chemiluminescence, electrochemiluminescence, bioluminescence, phosphorescence, radioactivity, magnetic field, or combinations thereof, and in a specific embodiment, the first and second detectable labels comprise an ECL label and the counting step can include measuring an ECL signal.

Embodiment (25): a method of detecting an analyte of interest in a sample comprising: (a) binding the analyte to: (i) a capture reagent on a surface comprising the capture reagent for the analyte; (ii) a first detection reagent for the analyte that is linked to a first nucleic acid probe; and (iii) a second detection reagent for the analyte that is linked to a second nucleic acid probe; thereby forming a complex on the surface comprising the binding reagent, the analyte and the first and second detection reagents; (b) using an extension process that requires the first and second probes to be in proximity, extending the second probe to form an extended sequence; and (c) measuring the amount of extended sequence bound to the surface. In this embodiment, the capture reagent is an antibody, antigen, ligand, receptor, oligonucleotide, hapten, epitope, mimitope, or an aptamer, e.g., the capture reagent is an antibody; the first detection reagent is an antibody, antigen, ligand, receptor, oligonucleotide, hapten, epitope, mimitope, or an aptamer, e.g., the first detection reagent is an antibody; the second detection reagent is an antibody, antigen, ligand, receptor, oligonucleotide, hapten, epitope, mimitope, or an aptamer; e.g., the second detection reagent is an antibody; and in a specific example, the capture reagent and the first and second detection reagents are antibodies to the analyte.

The extended sequence of embodiment (25) can include one or more detection sequences and the measuring step can include contacting the extended sequence with a plurality of labeled probes complementary to the one or more detection sequences; the extended sequence can include one or more modified bases and the measuring step can include contacting the extended sequence with a plurality of detectable moieties capable of binding to the one or more modified bases; and/or the extended sequence can include one or more labeled bases and the measuring step can include detecting the presence of the one or more labeled bases. The one or more modified bases comprise an aptamer, aptamer ligand, antibody, antigen, ligand, receptor, hapten, epitope, or a mimetope and the plurality of detectable moieties each comprise a binding partner of the one or more modified bases and a detectable label. The one or more modified bases can include streptavidin and the plurality of detectable moieties each comprise biotin and a detectable label; the one or more modified bases comprise biotin and the plurality of detectable moieties each comprise streptavidin and a detectable label; the one or more modified bases comprise avidin and the plurality of detectable moieties each comprise biotin and a detectable label; and/or the one or more modified bases comprise biotin and the plurality of detectable moieties each comprise avidin and a detectable label.

Step (a) of embodiment (25) can include binding the analyte to the following species in the following order: (i) the capture reagent on a surface; and (ii) the detection reagent for the analyte; binding the analyte to the following species in the following order: (i) the detection reagent for the analyte; and (ii) the capture reagent on the surface; or binding the analyte to the following species simultaneously or substantially simultaneously: (i) the capture reagent on a surface; and (ii) the detection reagent for the analyte. The extending step can include binding the probe to a template nucleic acid sequence and extending the probe by polymerase chain reaction; or binding the probe to a template nucleic acid sequence, forming a circular nucleic acid template, and extending the circular template by rolling circle amplification. In this embodiment, the extended probe can remain localized on the surface following probe extension, e.g., the complex remains bound to the surface after the extending step. The extending step can include PCR (Polymerase Chain Reaction), LCR (Ligase Chain Reaction), SDA (Strand Displacement Amplification), 3SR (Self-Sustained Synthetic Reaction), or isothermal amplification methods. In a specific example, the extending step can include isothermal amplification methods, e.g., helicase-dependent amplification or rolling circle amplification (RCA).

The extension process of embodiment (25) can comprise contacting the complex formed in step (a) with a connector sequence comprising (i) an interior sequence complementary to the second probe and (ii) two end sequences complementary to non-overlapping regions of the first probe. The process can further comprise ligating the two end sequences of the connector oligonucleotide to form a circular target sequence that is hybridized to both the first and second probes. The extension process of embodiment (25) can also include contacting the complex formed in step (a) with a first connector oligonucleotide sequence including a first connector probe sequence complementary to a first region of the first probe and a first region on the second probe, and a second connector oligonucleotide comprising a second probe sequence complementary to a second non-overlapping region of the first probe and a second non-overlapping region of the second probe. The process can also include ligating the first and second connector oligonucleotides to form a circular target sequence that is hybridized to both the first and second probes.

The surface of embodiment (25) can comprise a particle or an assay domain of an assay module such as a well of a multi-well plate or an assay chamber of a cartridge. The surface can include a plurality of distinct binding domains and the capture reagent(s) are located on two distinct binding domains on the surface. If the surface is a well, the well can include a plurality of distinct binding domains and the capture reagent(s) are located on two distinct binding domains within the well. The surface can include a plurality of distinct binding domains and the capture reagent(s) are located on the same binding domain on the surface, and if the surface is a well, the well can comprise a plurality of distinct binding domains and the capture reagent(s) are located on the same binding domain within the well. The surface can include an electrode and the measuring step can include applying a voltage waveform to the electrode to generate an electrochemiluminesce signal. The method optionally includes collecting the particle on an electrode and applying a voltage waveform to the electrode to generate an electrochemiluminescence signal. The measuring step may further comprise binding the extended sequence to a detection probe having a detectable label, measuring the detectable label and correlating the measurement to the amount of analyte in the sample, wherein the detection probe comprising a nucleic acid sequence that is complementary to a region of the extended sequence. The detectable label can be measured by a measurement of light scattering, optical absorbance, fluorescence, chemiluminescence, electrochemiluminescence, bioluminescence, phosphorescence, radioactivity, magnetic field, or combinations thereof. In a specific example, the detectable label is an ECL label and the measuring step can include measuring an ECL signal.

Embodiment (26): a kit for the detection of an analyte of interest in a sample comprising, in one or more vials, containers, or compartments: (a) a surface comprising a capture reagent for the analyte; (b) a first detection reagent for the analyte that is linked to a first nucleic acid probe; and (c) a second detection reagent for the analyte that is linked to a second nucleic acid probe.

The capture reagent of embodiment (26) can include an antibody, antigen, ligand, receptor, oligonucleotide, hapten, epitope, mimitope, or aptamer, e.g., the capture reagent can include an antibody; the first detection reagent can include an antibody, antigen, ligand, receptor, oligonucleotide, hapten, epitope, mimitope, or aptamer, e.g., the first detection reagent can include an antibody; the second detection reagent can include an antibody, antigen, ligand, receptor, oligonucleotide, hapten, epitope, mimitope, or aptamer, e.g., the second detection reagent can include an antibody; and the surface can include a particle and/or a well of a multi-well plate. The surface can include a plurality of distinct binding domains and the capture reagent(s) are located on two distinct binding domains on the surface; and if the surface is a well, the well can comprise a plurality of distinct binding domains and the capture reagent(s) are located on two distinct binding domains within the well. Optionally, the surface can include a plurality of distinct binding domains and the capture reagent(s) are located on the same binding domain on the surface, and if the surface is a well, the well can include a plurality of distinct binding domains and the capture reagent(s) are located on the same binding domain within the well. The surface can comprise an electrode.

The surface of embodiments 1-26 can include an interior surface of an assay container, e.g., a test tube, cuvette, flow cell, FACS cell sorter, cartridge, or an assay domain of an assay module such as a well of a multi-well plate or an assay chamber of a cartridge. The surface can also comprise a slide, assay chips, or assay array; a pin, probe, bead, or filtration media; lateral flow media, e.g., a filtration membrane.

Embodiment (27): a method of detecting an analyte of interest in a sample comprising one or more analyte molecules, the method comprising: (a) contacting the sample with a surface comprising a plurality of resolvable binding regions positioned on the surface, each resolvable binding region comprising a plurality of capture reagents for one or more analyte molecules in the sample; (b) binding one or more analyte molecules to (i) one or more capture reagents on the surface; (ii) a first detection reagent for the analyte comprising a first detectable label, and (iii) a second detection reagent for the analyte comprising a second detectable label; thereby forming a detection complex on a resolvable binding domain on the surface comprising the capture reagent, the analyte and the first and second detection reagents, wherein the first and second detectable labels are different label compounds; (c) determining the presence or absence of the analyte molecule in each binding region; and (d) identifying the number of binding regions that contain the analyte molecule and/or the number of binding regions that do not contain the analyte molecule. The identifying step can include imaging an optical signal from the surface to generate an image comprising a plurality of pixels and each resolvable binding region maps to one or more pixels in the image. The resolvable binding regions can be elements of an array and/or configured to isolate individual particles. Each resolvable binding region can be an individual nano-wells having a volume <100 nL and/or at least 99% of the binding regions contain either zero or one analyte molecule; at least about 95% of the binding regions contain either zero or one analyte molecule; at least about 80% of the binding regions contain either zero or one analyte molecule; or at least about 50% of the binding regions contain either zero or one analyte molecule. The concentration of analyte molecules in the sample can be determined at least in part using a calibration curve, a Poisson distribution analysis and/or a Gaussian distribution analysis of the number of binding regions that contain at least one or one analyte molecule.

The surface of embodiment (27) can include a plurality of particles each comprising a plurality of capture reagents for an analyte molecule wherein the plurality of particles is distributed across a plurality of resolvable binding regions, and the method can include: (i) binding the one or more analyte molecules to one or more capture reagents on the surface, and first and second detection reagents for each of the one or more analyte molecules, wherein the first and second detection reagents include first and second detectable labels, respectively; (ii) distributing the plurality of particles across an array of resolvable binding regions; and (iii) determining the presence or absence of an analyte molecule in each resolvable binding regions, so as to identify the number of binding regions that contain an analyte molecule and/or the number of binding regions that do not contain an analyte molecule, wherein optionally, each resolvable binding region is an individual nano-wells having a volume <100 nL, and/or at least 99% of the binding regions contain either zero or one analyte molecule; at least about 95% of the binding regions contain either zero or one analyte molecule; at least about 80% of the binding regions contain either zero or one analyte molecule; and/or at least about 50% of the binding regions contain either zero or one analyte molecule.

The capture reagent in embodiment (27) is an antibody, antigen, ligand, receptor, oligonucleotide, hapten, epitope, mimitope, or an aptamer, e.g., the capture reagent is an antibody; the first detection reagent is an antibody, antigen, ligand, receptor, oligonucleotide, hapten, epitope, mimitope, or an aptamer, e.g., the first detection reagent is an antibody; the second detection reagent is an antibody, antigen, ligand, receptor, oligonucleotide, hapten, epitope, mimitope, or an aptamer, e.g., the second detection reagent is an antibody. In a specific example, the capture reagent and the first and second detection reagents are antibodies to the analyte.

Step (a) of embodiment (27) can include binding the analyte to the following species in the following order: (i) the capture reagent on a surface; and (ii) the first and second detection reagents for the analyte; binding the analyte to the following species in the following order: (i) the first and second detection reagents for the analyte; and (ii) the capture reagent on the surface; or binding the analyte to the following species simultaneously or substantially simultaneously: (i) the capture reagent on a surface; and (ii) the first and second detection reagents for the analyte.

The surface of embodiment (27) can include a particle or an assay domain of an assay module such as a well of a multi-well plate or an assay chamber of a cartridge. In a specific example, the surface can include an electrode and the identifying step can include applying a voltage waveform to the electrode to generate an electrochemiluminesce signal. The method of embodiment (27) can further include collecting the particle on an electrode and applying a voltage waveform to the electrode to generate an electrochemilumin-escence signal. The first detectable label is measured by a measurement of light scattering, optical absorbance, fluorescence, chemiluminescence, electrochemiluminescence, bioluminescence, phosphorescence, radioactivity, magnetic field, or combinations thereof; and/or the second detectable label is measured by a measurement of light scattering, optical absorbance, fluorescence, chemiluminescence, electrochemiluminescence, bioluminescence, phosphorescence, radioactivity, magnetic field, or combinations thereof. The first and second detectable labels can be measured independently, and in one example, the first and second detectable labels are luminescent labels that differ from one another with respect to spectral properties.

The surface of embodiment (27) can include an interior surface of an assay container, e.g., a test tube, cuvette, flow cell, FACS cell sorter, cartridge, or an assay domain of an assay module such as a well of a multi-well plate or an assay chamber of a cartridge. The surface can also comprise a slide, assay chips, or assay array; a pin, probe, bead, or filtration media; lateral flow media, e.g., a filtration membrane.

Embodiment (28): a kit for the detection of an analyte of interest in a sample comprising one or more analyte molecules, the kit comprising: (a) a surface comprising a plurality of resolvable binding regions positioned on the surface, each resolvable binding region comprising a plurality of capture reagents for one or more analyte molecules in the sample; (b) a first detection reagent for the analyte comprising a first detectable label, and (c) a second detection reagent for the analyte comprising a second detectable label; wherein the first and second detectable labels are different label compounds.

The resolvable binding regions of embodiment (28) can be elements of an array and/or configured to isolate individual particles. Each resolvable binding region is optionally, an individual nano-wells having a volume <100 nL. The surface can include a plurality of particles each comprising a plurality of capture reagents for an analyte molecule wherein the plurality of particles is distributed across a plurality of resolvable binding regions, and the kit can include: first and second detection reagents for each of the one or more analyte molecules, wherein the first and second detection reagents include first and second detectable labels, respectively.

The capture reagent in embodiment (28) is an antibody, antigen, ligand, receptor, oligonucleotide, hapten, epitope, mimitope, or an aptamer, e.g., the capture reagent is an antibody; the first detection reagent is an antibody, antigen, ligand, receptor, oligonucleotide, hapten, epitope, mimitope, or an aptamer, e.g., the first detection reagent is an antibody; the second detection reagent is an antibody, antigen, ligand, receptor, oligonucleotide, hapten, epitope, mimitope, or an aptamer, e.g., the second detection reagent is an antibody. In a specific example, the capture reagent and the first and second detection reagents are antibodies to the analyte.

The surface of embodiment (28) can include a particle or an assay domain of an assay module such as a well of a multi-well plate or an assay chamber of a cartridge. In a specific example, the surface can include an electrode and the identifying step can include applying a voltage waveform to the electrode to generate an electrochemiluminesce signal. The first detectable label is measured by a measurement of light scattering, optical absorbance, fluorescence, chemiluminescence, electrochemiluminescence, bioluminescence, phosphorescence, radioactivity, magnetic field, or combinations thereof; and/or the second detectable label is measured by a measurement of light scattering, optical absorbance, fluorescence, chemiluminescence, electrochemiluminescence, bioluminescence, phosphorescence, radioactivity, magnetic field, or combinations thereof. The first and second detectable labels can be measured independently, and in one example, the first and second detectable labels are luminescent labels that differ from one another with respect to spectral properties.

The surface of embodiment (28) can include an interior surface of an assay container, e.g., a test tube, cuvette, flow cell, FACS cell sorter, cartridge, or an assay domain of an assay module such as a well of a multi-well plate or an assay chamber of a cartridge. The surface can also comprise a slide, assay chips, or assay array; a pin, probe, bead, or filtration media; lateral flow media, e.g., a filtration membrane.

Reference is made to specific examples illustrating the embodiments above. It is to be understood that the examples are provided to illustrate rather than limit the scope of various embodiments of the invention.

EXAMPLES

Methods

Boxer Recruitment, Consent and Sample Collection, GFAP Quantification, and APOE Genotyping All aspects of the study described were approved by the institutional review board (IRB) at UT Southwestern Medical Center (Dallas, Texas) prior to the initiation of any study-specific procedures. Boxers were randomly recruited through North Texas boxing training centers and IRB-approved consent was obtained. We administered the Immediate Post-Concussion Assessment and Cognitive Testing [ImPACT], Hopkins Verbal Learning Test-Revised [HVLT-R]. We only enrolled athletes that exhibited normal baseline neuropsychological scoring (based on national averages of healthy age-matched adults) and that were absent of symptoms of neurological or mood deficits. Blood, demographics and boxing history were acquired from each boxer.

Once informed consent was obtained from the athlete, blood was collected once at baseline (within 2 weeks of competition) and ~30 minutes after the end of the competition (day 1). In brief, at each time-point 8 cc of blood was collected and centrifuged at 4 degrees Celsius for 10 minutes at 1500 rpm. The plasma and buffy coat was collected and aliquoted into 1 ml tubes and immediately frozen at −80 degrees Celsius. Genomic DNA extracted by standard protocols. Genotypes were determined by Taqman assays (Applied Biosystems, Inc; Foster City, CA). Details regarding genotyping methods have been published previously.[12, 13]

To elucidate differences between non-APOE4 and APOE4 expressers, with respect to GFAP plasma levels, we measured GFAP in a subset (n=25) of active boxers. The plasma samples were analyzed by Meso-Scale Diagnostics, LLC. (MSD) for measurement of GFAP using an immunoassay developed in part through work supported by US Army Medical Research and Materiel Command (contract W81XWH-13-C-0196). Plasma levels of GFAP were quantified using electrochemiluminescence (ECL) detection in an array-based multiplex format. Briefly, capture antibody for GFAP was printed on an electrode array spot within the wells of 98-well MULTI-ARRAY® plates. Detection antibody was conjugated with electrochemiluminescent SULFO-TAG™. In order to reduce background and reduce heterophilic antibody interference, diluents contained various blockers including purified mouse immunoglobulin. Plates were read in a SECTOR® Imager 6000 reader. The samples were tested in duplicate. The detection limit was estimated as 2.5 standard deviations above the background level. The calibration curve also was used to estimate the upper limit of the immunoassay's linear range. The final reported concentration of GFAP was the mean of two replicates.

Neuropsychological/mood assessments and blood were collected as recommended by the National Institutes of Health (NIH) NINDS Common Data Elements (CDE). Recruitment, testing and genotyping were conducted by JG, JK, JM, MS, RH, and L-YC.

Inclusion Criteria

1. Professional boxers between 18-40 years old
2. Both men and women
3. Blunt head injury
4. Subject has provided full written consent prior to the performance of any protocol-specified procedure Exclusion Criteria 1. Participants with cognitive/psychological disorders
2. Recognized spinal cord injury
3. Known inclusion in an interventional clinical trial
4. Known history of alcohol/drug abuse Control Cohort Selection A number of epidemiological studies on Alzheimer's disease (AD) risk have collected and published data on APOE genotype on subjects from around the world. 14 Our Texas boxer cohort consisted of two distinct demographic groups with an average age of 24. A limitation of many APOE studies is that the target population is an aged population, and the results are striated into Alzheimer's disease and non-Alzheimer's disease populations. For this study we required a control group that reported on at least one of our demographic group and was inclusive of young people. The Hanis et al study[15] reports on a Hispanic population of 963 Mexican-Americans living in Texas, with random sampling involving a strategy of random block selection and dwelling unit enumeration to identify a representative sample of the population. Within selected dwelling units, only one individual aged 15-74 years was randomly selected for a complete physical evaluation. The selection criteria used resulted in a random sampling of the population, and 63% of the cohort was aged under 44 y.[16]

mTBI and CCI Procedure

This study was carried out in strict accordance with the recommendations in the Guide for the Care and Use of Laboratory Animals of the National Institutes of Health. The protocol was approved by the Institutional Animal Care and Use Committee at Georgetown University. Humanized APOE3 and APOE4 mice were exposed to single or repeat mTBI as described previously.[11] Mice were anesthetized with 3% isoflurane in oxygen for 120s in an induction chamber, and then transferred to the injury device where they continued breathing anesthetic through a pliable/non-fixed nose cone for a further 60s. There was no skin deflection or surgery of any kind. The mouse head was positioned on the gel pad so that the flat surface of the skull was presented perpendicular to the impactor tip and the ears were held away from the impact site with tape. The impactor tip was lowered to the surface of the mouse head, retracted and manually dialed down to the required deflection depth. Following impact at 2.35 m/sec, mice were removed from isoflurane and placed on their backs. The latency to return of righting reflex was determined and used as the primary measure of injury severity. The latency until spontaneous ambulation (a mouse taking 3 consecutive steps) was also quantified. For repeat mTBI experiments, mice received 1 mTBI per day, 5 days a week for 6 weeks. DZ designed and built the mTBI device. CW and MP were responsible for mTBI procedures and data capture.

Dendritic Spine Analysis

Mice were anesthetized and transcardially perfused with phosphate buffered saline (PBS). A hemibrain was fixed and prepared for Golgi staining using the FD Rapid Golgi Stain Kit (FD NeuroTechnologies, Ellicott City, MD), as previously reported.[11, 17] The brains were randomly coded before fixation, and the resulting sections and images remained coded to ensure blinded assessment. 150 μm sections were prepared, bright-field microscopy images of pyramidal neurons in Layer II/III of the cortex were captured, and the number of dendritic spines on apical oblique (AO) dendrites was quantified. AO dendrites project off the apical dendrite, and our counts only incorporated primary AO dendrites. We counted spines in a 20 μm section of the primary AO. CW and AN conducted the image capture and spine counts using Image J Software (National Institutes of Health, Bethesda, Maryland).

Immunostaining and Quantification

Mice were anesthetized and transcardially perfused with phosphate buffered saline (PBS) and hemibrains were drop-fixed in 4% paraformaldehyde (PFA) overnight before cryoprotection in 30% sucrose for 48 hours. Brains were cut in 40 μm-thick sections using a microtome and were stored free-floating in cryoprotectant solution. Prior to immunostaining, sections were incubated in 0.3% $H_2O_2$ and blocked with 3% normal goat serum (NGS) in PBS with 0.25% Triton X-100 (PBS-TX), and incubated in PBS-TX and 1% NGS with primary antibody. Rabbit polyclonal anti-Iba-1 (1:5000, Wako Chemicals, Richmond, VA; Cat. #019-19741) and biotinylated goat anti-rabbit (1:2000, Vector Labs, Burlingame, CA; Cat. #BA-100) in PBS-TX (0.25%), followed by the Vectastain Avidin/Biotinylated enzyme Complex (ABC) kit (1:400, Vector Laboratories, Burlingame, CA; Cat #PK-6100) and 3,3'-Diaminobenzidine (DAB) (Sigma) substrate to visualize primary antibodies.

Histological sections were assessed for staining in the regions covering the entire optic tract (−2.18 mm to −2.70 mm Bregma). Every fourth coronal section of the optic tract was selected, yielding at least 4 sections collected per animal. From each section, three distinct fields within the optic tract were randomly selected and four images of sequential optical z sections were obtained from each field. Images from each field were combined into a single overlay image, and Iba-1 positive cells were counted using the overlay. Helicon Focus software (version 3.2) was used for three-dimensional reconstruction of z sections thickness. The total number of Iba-1 positive cells was expressed per mm2. Bushy microglial cells were identified by short thick processes, few branches, and larger cell body volume.[11, 18] Tissue staining by MP, imaging and analysis by SV.

Statistics

Statistical analysis was performed using Graphpad Prism Version 5.0f. Two-Way ANOVA with Bonferroni post-hoc analysis was used for all preclinical data, with the exception of panel 2D, where a Two-Way Repeated Measures ANOVA was used. In Table 2 a Fisher's Exact Test was used to compare boxers to control data. Statistical analysis by MB.

Results

The APOE4 Allele is Overrepresented in a Professional Boxer Cohort

For this study we randomly recruited 60 young, active, asymptomatic professional boxers in Texas. All boxers tested within the normal range on the Immediate Post-Concussion Assessment and Cognitive Testing [ImPACT] and the Hopkins Verbal Learning Test-Revised [HVLT-R]. Gender distribution, age and ethnicity are outlined in Table 1. The frequency of the APOE4 allele has been best documented in aging Caucasians, with an allele frequency of 14% and a prevalence of 25%.[14] In our cohort of Texas boxers, the APOE4 allele frequency was 22.5%. APOE4 prevalence was 38.3%, with 31.6% heterozygous and 6.7% homozygous for APOE4.

In African populations there is a natural variance in APOE4 frequency depending on genetic background,[19] so in order to perform a controlled comparison we restricted our analysis to Hispanic boxers and compared them to a published dataset of 963 Texan Hispanics who were primarily under the age of 44 y.[15] We report that Hispanic boxers have a 117% increase in the overall frequency of APOE4 compared to controls (P=0.0042), a 79% increase in APOE4 heterozygotes (P=0.043), and a 418% increase in APOE4 homozygotes (P=0.069, n.s.) (Table 2). Overall the prevalence of the APOE4 allele increased from 19.2% in controls to 38.2% in Hispanic professional boxers (P=0.0136).

Plasma GFAP Levels are Lower in APOE4-Positive Boxers

Figure 1B:
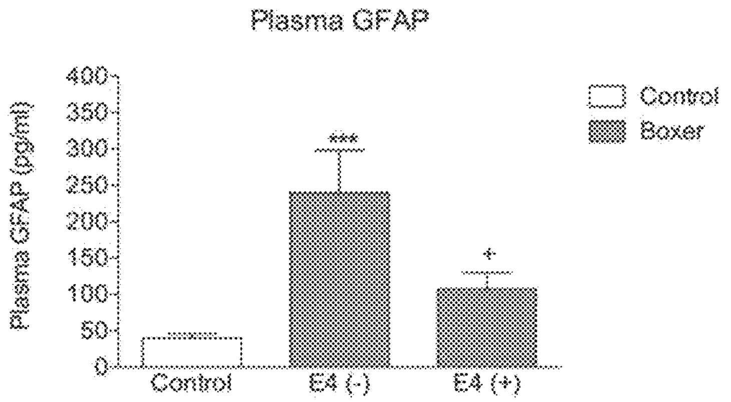

We collected plasma from active boxers and from a non-brain injury cohort of 21 healthy controls. We found that plasma GFAP was 405% higher in the active boxers compared to the control cohort (P<0.001; FIG. 1A). There was an effect of APOE4 status amongst boxers, with levels of GFAP in APOE4-positive boxers not significantly different to controls, and significantly lower than APOE4-negative boxers (P<0.05; FIG. 1B).

APOE4 Mice have Larger Lesion Size after Severe TBI

Figures 2A, 2B, 2C, 2D, 2E:
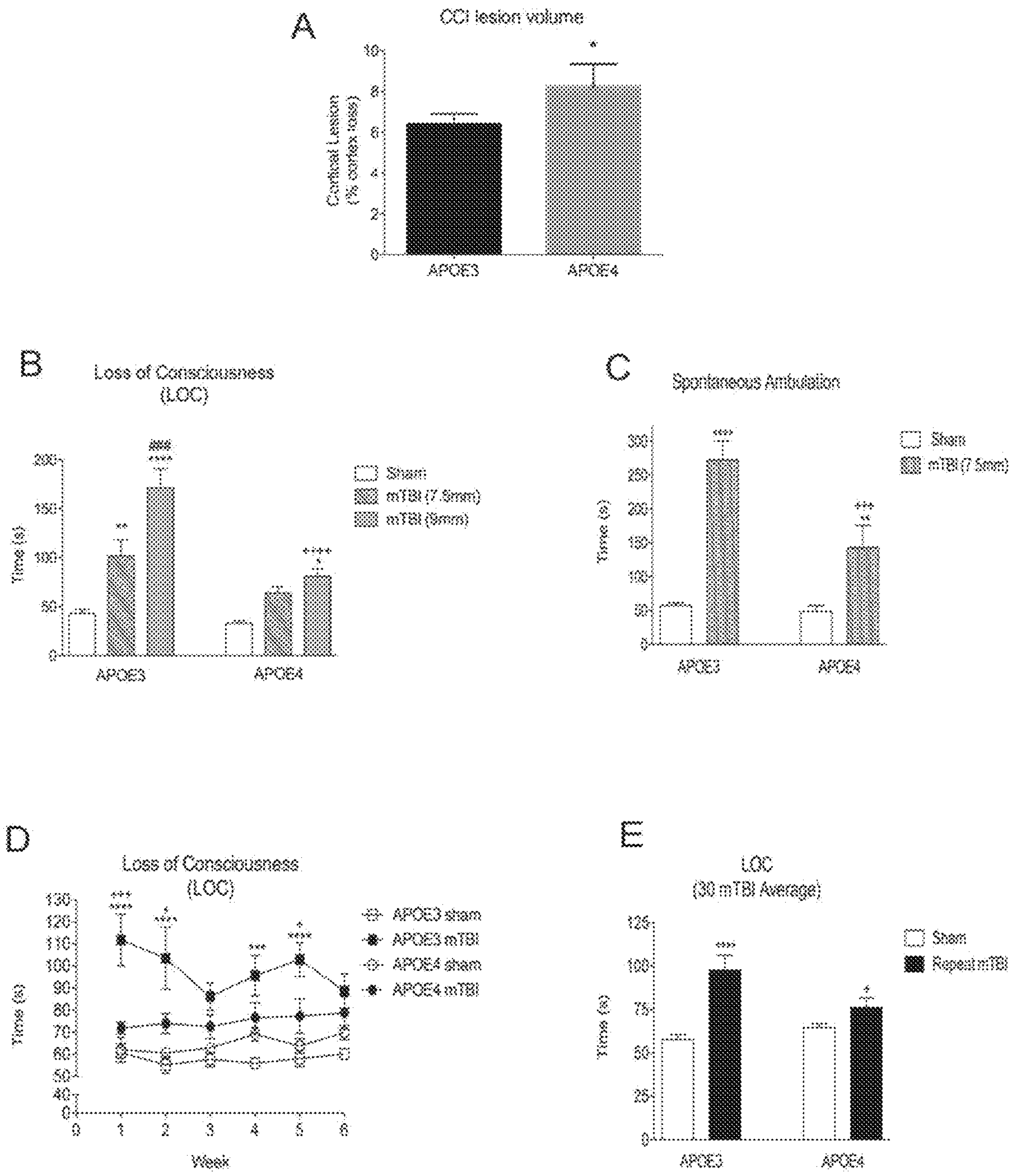
FIGS. 2A-E show that APOE4 improves arousal and ambulation time after single or repeat mTBI. A) Cortical tissue loss after controlled cortical impact (CCI) was quantified at 28d post-injury in APOE3 versus APOE4 mice. N=5. Unpaired t-test (*=P<0.05). B) Loss of consciousness (LOC) following mTBI as determined by the latency in seconds to the return of the righting reflex. 7.5 mm and 9 mm refer to the amount of head deflection occurring with impact. N=9-10 per group. Two-Way ANOVA with Bonferroni post-test. (*=P<0.05, =P<0.01, =P<0.0001 vs genotype sham; ## #=P<0.001 vs APOE3 mTBI (7.5 mm); ++++=P<0.0001 vs APOE3 mTBI (9 mm)). C) Latency to the return of spontaneous ambulation following a single 7.5 mm mTBI. N=9-10 per group. Two-Way ANOVA with Bonferroni post-test. (=P<0.01, **=P<0.0001 vs genotype sham; +++=P<0.001 vs APOE3 mTBI). D) LOC following repeat mTBI. Mice received 1 mTBI per day, 5 days per week, for 6 weeks. LOC was determined by using latency in seconds to the return of the righting reflex. For each animal, the 5 LOC readings per week were averaged into a single timepoint to smooth the data and reduce the effects of daily variability. N=18-20. Two-Way Repeated Measures ANOVA with Bonferroni post-test. (*=P<0.001, **=P<0.0001 vs genotype sham at the matching timepoint; +=P<0.05, +++=P<0.001 vs APOE4 mTBI at the matching timepoint). E) Average daily LOC from APOE mice following 30 mTBI over 6 weeks. N=18-20. Two-Way ANOVA with Bonferroni post-test. (**=P<0.0001 vs genotype sham; +=P<0.05 vs APOE3 mTBI).

We exposed mice to a severe TBI using controlled cortical impact, and quantified lesion size at 28d post-trauma. Lesion size in APOE4 mice was 29% larger compared to APOE3 mice (P<0.05; FIG. 2A).

APOE4 Mice have Faster Arousal Times after Single and Repeat mTBI

We next examined how APOE genotype affected the acute response to mTBI. Mice were exposed to 3 minutes of 3% isoflurane anesthesia and a single mTBI with a head deflection of either 0 mm (sham), 7.5 mm, or 9 mm and LOC was determined by quantifying the righting reflex (FIG. 2B). APOE3 mice had a significant LOC compared to APOE3 sham mice, with a LOC of 102s with 7.5 mm head deflection (P<0.01 vs sham), and an LOC of 171s with 9 mm deflection (P<0.0001 vs sham). The arousal response in APOE4 mice was faster compared to APOE3 mice. The 7.5 mm head deflection did not significantly increase LOC time compared to APOE4 sham, and the 9 mm head deflection caused a 81s LOC (P<0.05 vs sham; P<0.0001 vs APOE3 9 mm). We also quantified the time for spontaneous ambulation to return in a separate cohort of 7.5 mm mice, and found that APOE4 mice display a faster return of spontaneous ambulation after mTBI (FIG. 2C).

To examine the arousal response after repeat mTBI, we exposed mice to a single mTBI per day, 5 days per week, for 6 weeks (total of 30 mTBI). The difference in LOC between APOE mice was maintained as the numbers of impacts were increased to thirty mTBI, with APOE3 mice displaying LOC significantly higher than sham APOE3 mice (P<0.0001). APOE4 mice did not exhibit elevated LOC at any timepoint, and they had faster arousal times after impact compared to APOE3 mice (P<0.05; FIG. 2D, 2E).

APOE4 Mice have Faster Arousal Times after Single and Repeat mTBI

Figures 3A, 3B, 3C:
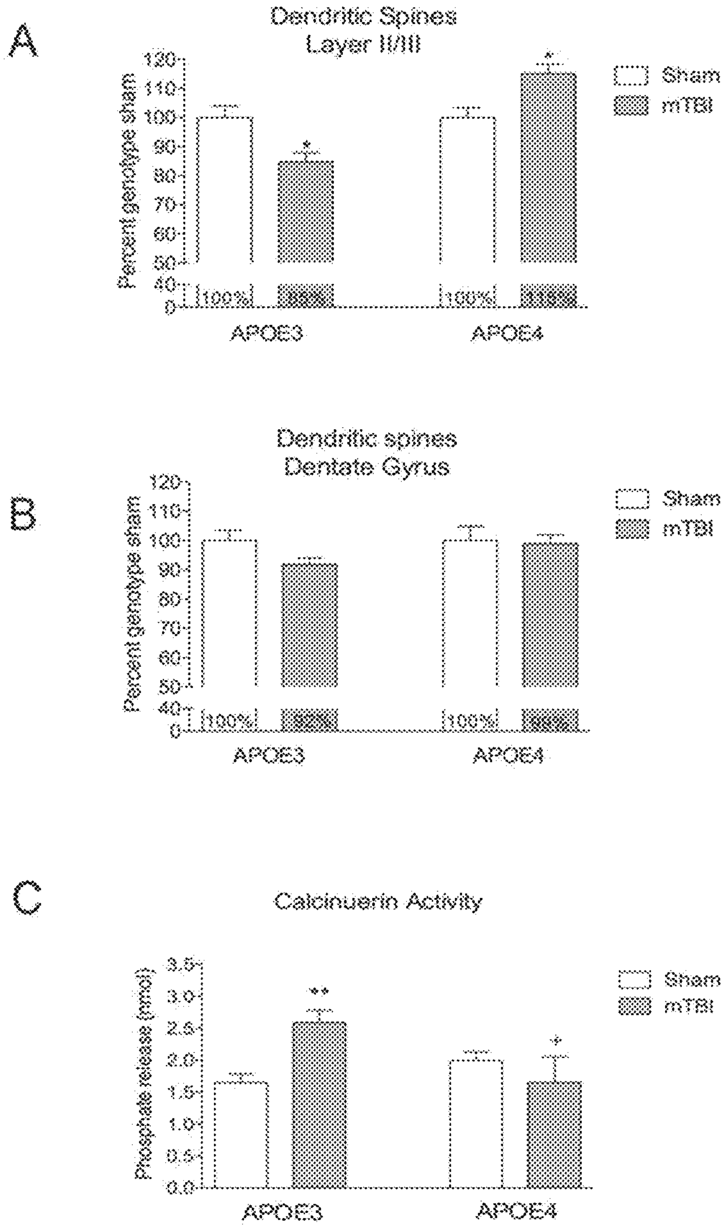
FIGS. 3A-C show that mTBI causes dendritic spine loss in APOE3, but not APOE4 mice. A) Dendritic spine number in the apical oblique dendrites of cortical Layer II/III neurons in APOE3 and APOE4 mice 24 h following single mTBI. Sham APOE4 mice have significantly lower numbers of dendritic spines than sham APOE3 mice (10.29±0.35 vs 11.86±0.47 spines/20 μm; P<0.05). To allow for comparison of spine changes in different genotypes after TBI the final spine number was normalized to the relevant genotype sham. N=35-63 neurons from 5 mice per group. Two-Way ANOVA with Bonferroni post-test (*=P<0.05 vs genotype sham; ++++=P<0.0001 vs APOE3 single mTBI; +++=P<0.001 vs APOE3 repeat mTBI). B) Dendritic spine number in the dentate gyrus in APOE3 and APOE4 mice 24 h following a single mTBI. Sham APOE3 mice have similar numbers of dendritic spines compared to sham APOE4 mice (21.43±0.75 vs 20.86±0.99; n.s.). To allow for comparison of spine changes in different genotypes after TBI the final spine number was normalized to the relevant genotype sham. N=54-82 neurons per group. C) Calcineurin activity was quantified by a phosphate release activity assay. N=5 per group. Two-Way ANOVA with Bonferroni post-test. (**=P<0.01 vs genotype sham; +=P<0.05 vs APOE3 mTBI).

We next examined how APOE genotype affects dendritic spine loss after a single or repeat mTBI. We have previously reported that a single mTBI causes a loss of cortical spines in C57/BI6 mice.[11] Here we find that single mTBI in APOE3 mice causes a 16% decrease in Layer II/III dendritic spines compared to sham APOE3 mice (P<0.05; FIG. 3*a*). We confirmed that sham APOE4 mice have lower spine numbers in Layer II/III compared to APOE3 sham mice (13% lower; APOE3 sham vs APOE4 sham; P<0.05; data not shown), as has been previously reported.[20] In contrast to APOE3 mice, mTBI did not cause a reduction in spine number in Layer II/III, but instead induced spine growth at 24 h post-injury (15% increase; P<0.05 vs APOE4 sham; FIG. 3A).

We also quantified dendritic spines in the dentate gyrus of the hippocampus and found that single mTBI caused a 9% loss of spines in APOE3 mice, but no loss of spines in APOE4 mice—however this decrease in APOE3 mice did not reach significance (FIG. 3B).

One pathway that controls dendritic spine loss is the calcium/calmodulin-dependent phosphatase calcineurin. We quantified calcineurin activity and found that in APOE3 mice there was a 57% increase in activity at 1d post-injury (P<0.01; FIG. 3C). Basal calcinuerin activity was 21% higher in APOE4 sham mice compared to APOE3 sham mice (n.s.), however mTBI did not cause an increase in calcineurin activity at 1d post-injury (FIG. 3C).

APOE4 Increases Optic Tract Inflammation after Repeat mTBI

Figures 4A, 4B, 4C, 4D:
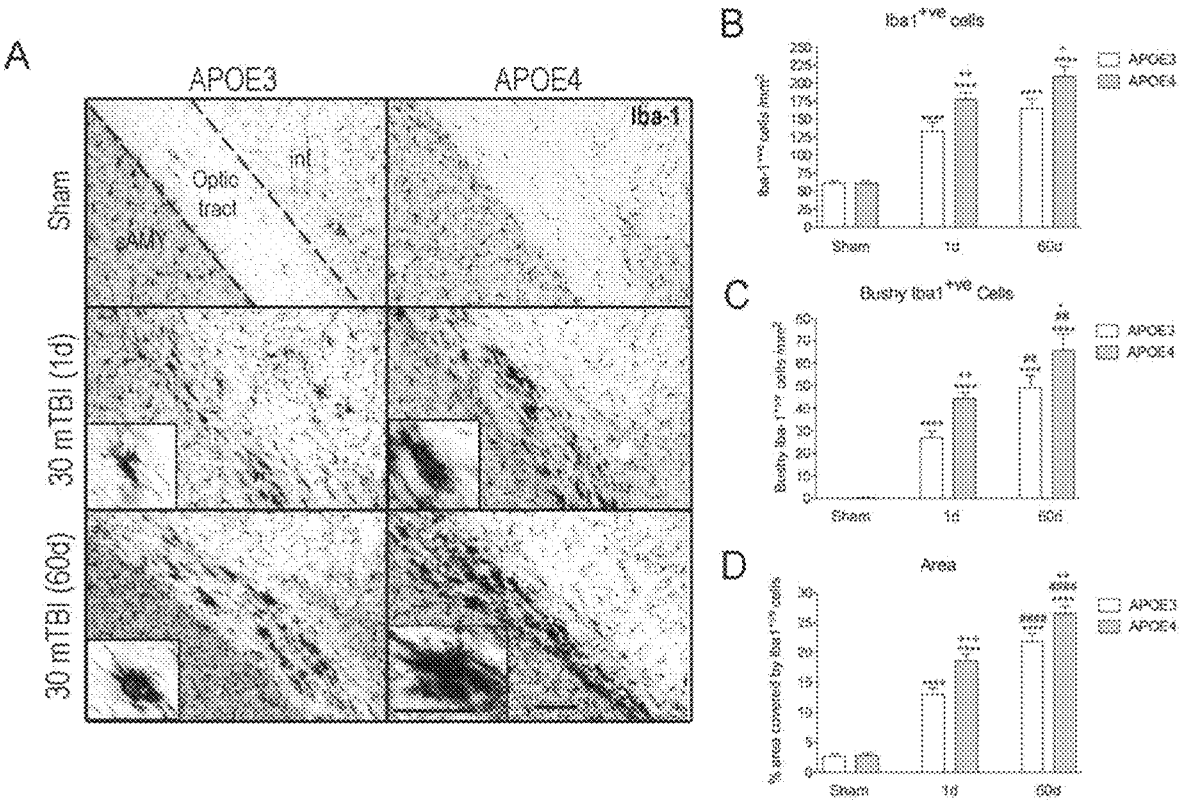
FIGS. 4A-D show that repeat mTBI causes chronic optic tract inflammation in both APOE3 and APOE4 mice. A) Iba1 staining of microglia/macrophage cells in the optic tract of sham mice 1d following the final sham procedure and repeat mTBI mice at 1d and 60d after the final injury. There was no difference between sham mice at 1d compared to 60d post-sham procedure (not shown). Representative image from 7-8 mice per group. Scale bars=50 μm (20 μm in inset). sAMY=striatum-like amygdalar nuclei; int=internal capsule B) Total number of Iba1+ve cells per mm2 of optic tract 1d and 60d after 30 mTBI. N=7-8. C) Total number of Iba1+ve cells with bushy morphology at 1d and 60d after 30 mTBI. N=7-8. D) Percent area of optic tract covered by Iba1+ve cells 1d and 60d after 30 mTBI. N=7-8. For G-I a Two-Way ANOVA with Bonferroni post-test was used. (****=P<0.0001 vs genotype sham; +=P<0.05, ++=P<0.01, +++=P<0.001 vs APOE3 mTBI at the same timepoint; ##=P<0.01, ####=P<0.0001 vs genotype 1d timepoint).
Figure 5:
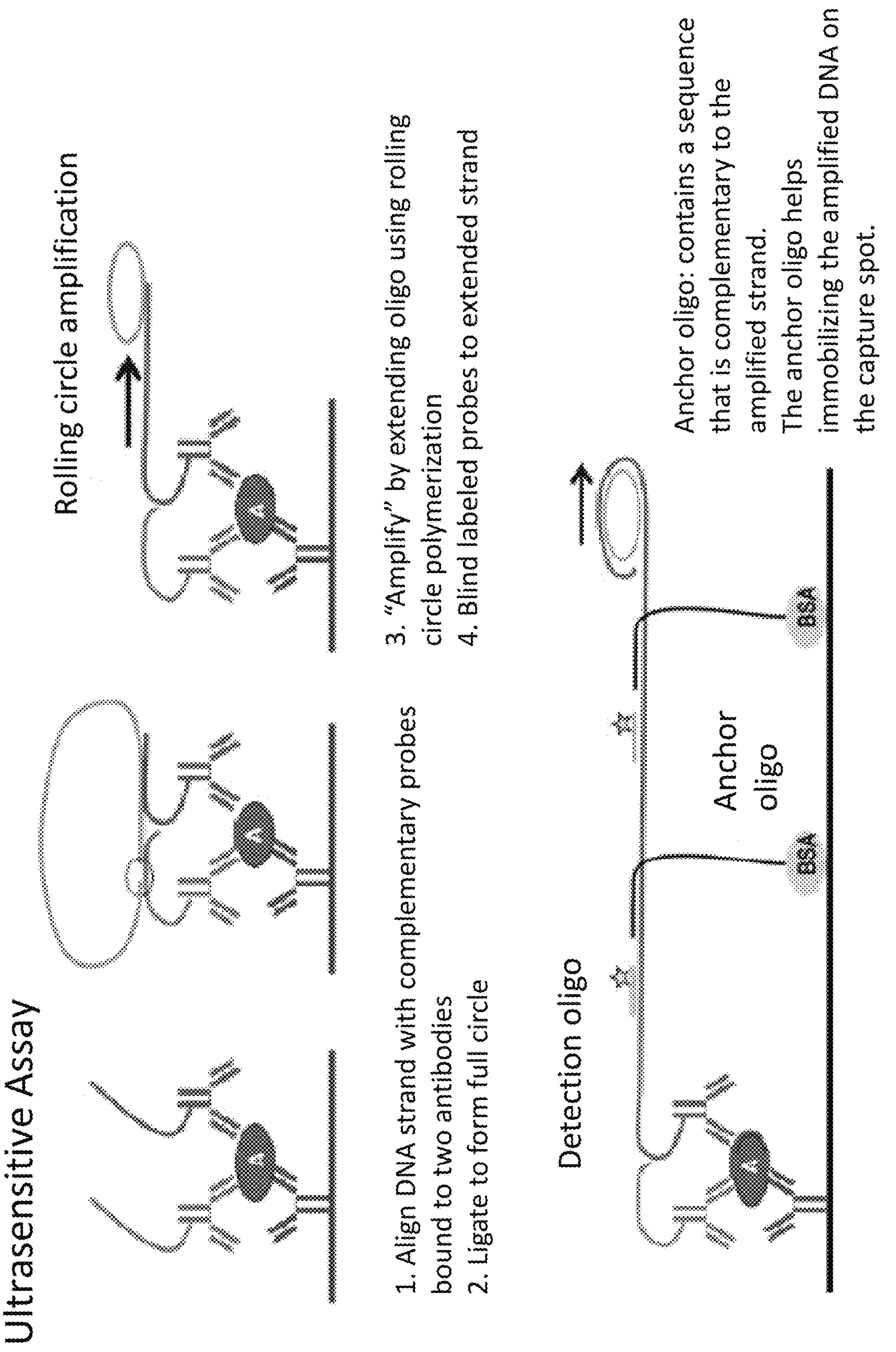
FIG. 5 is an embodiment of the Ultrasensitive Assays.

Repeat mTBI causes white matter inflammation that is focused in the optic tract. We examined the effect of APOE genotype on optic tract inflammation at 1d and 60d following the final mTBI. Both genotypes displayed white matter inflammation that persisted and progressed through 2 m post-trauma (FIG. 4A). The total number of Iba1-positive cells in the optic tract was enhanced by repeat mTBI (FIG. 4B), as were the number of microglial cells with a bushy morphology (FIG. 4C), and the total size of the microglia (FIG. 4D). At both the 1d and 60d timepoints, the number of $Iba1^{+ve}$ microglial/macrophages, number of bushy $Iba1^{+ve}$ cells, and area of the optic tract covered by $Iba1^{+ve}$ cells were all significantly higher in APOE4 mice following repeat mTBI compared to APOE3 mice (FIG. 4B-D).

Discussion

In the current study, we provide evidence that the APOE4 allele is overrepresented in a cohort of young, professional boxers, and that APOE4-positive boxers have lower levels of plasma GFAP compared to non-carriers. Overrepresentation of a genetic polymorphism suggests that this allele may be providing an advantage to pugilists. In order to study if this genetic polymorphism conveys resilience to head trauma, we studied the response of APOE humanized mice to single and repeat mTBI and found that APOE4 had improved acute responses to head trauma compared to APOE3 mice, but had worse chronic neuroinflammation following repeat mTBI.

The frequency of the APOE4 allele has been best documented in aging Caucasians, with an allele frequency of 14% and a prevalence of 25%.[14] However studies show that allele frequency fluctuates depending on ethnicity, with Hispanic populations having less APOE4 than Caucasians, and those of African ancestry with higher APOE4.14 Here we report that APOE4 frequency and prevalence is high in professional boxers with 38% carrying at least once copy of the APOE4 allele. When Hispanic boxers are compared to a non-boxing ethnically matched control population the frequency and prevalence of APOE4 is double that of controls. This was an unexpected finding, however a very recent report on the effect of APOE status on cognition and brain structure in professional fighters also lists the APOE4 status of their subjects. Close examination of the data reveals that, similar to our data, 35% of active boxers in that cohort also carry the APOE4 allele (n=77),[21] as well as 38% of mixed fighters (n=18). This association was not apparent in active mixed-martial arts fighters (22%, n=72).[21]

The reasons why APOE4 allele is enriched in cohort of young, active, professional boxers are not immediately clear, but genetic resilience may be a factor. While multiple elements are required to produce a successful boxer, the ability to remain asymptomatic after head trauma should enrich for a resilience allele as those with frequent/severe symptoms drop the sport. However even if the APOE4 can provide resilience, it is clear that APOE4 does not fully protect against concussion as it is well documented that APOE4 carriers can be concussed, do suffer from post-concussion syndrome, and can develop the chronic pathology/symptoms of CTE.[5, 6]

Based on previous literature on the effect of the APOE4 allele on outcome after preclinical TBI,[7, 9, 22] including our data in this study, we had hypothesized that the APOE4 allele would also have a detrimental effect on outcome after mTBI. Instead our data revealed that APOE4 mice have faster arousal times after mTBI, with a quicker latency to the return of the righting reflex after mTBI and quicker return of locomotion after mTBI. This effect is unexpected, given that the presence of APOE4 has been shown to increase coma time in human TBI subjects.[1] The apoE protein is a multi-faceted protein with important roles in amyloid clearance after TBI,[9] synaptic plasticity,[20] cholesterol transport,[23] and cell survival.[23] With such diverse roles it is unsurprising how detrimental a loss-of-function polymorphism such as the APOE4 allele can be to outcome after severe TBI. However, mTBI is a very different type of injury to moderate-to-severe TBI. Using animal models we have shown that traumatic axonal injury (TAI) is a hotspot of Aβ4 and p-tau production after severe TBI,[24, 25] however in our mTBI model there is no TAI and so no acute or chronic increase in amyloid or p-tau.[11] Similarly, there is no evidence of acute apoptotic cell death or neuroinflammation in grey matter in our mTBI model.[11] With an absence of “classical” TBI pathology that may overwhelm more subtle differences, it is instead important to identify factors that contribute to changes in consciousness and arousal following injury. Previous studies implicate cholinergic neurons associated with the reticular activating system (RAS) as being activated at moments of unconsciousness,[26, 27] and multiple studies have shown that there is an interaction between APOE genotype and the cholinergic system including decreased cholinergic neuron activity in the basal forebrain of APOE4 Alzheimer's subjects[28] and reduced evoked acetylcholine release from the hippocampus of APOE4 mice.[29] Impaired release of acetylcholine in the brainstem in response to mTBI could explain the rapid arousal of APOE4 mice to head injury.

mTBI causes a temporary reduction in excitatory synapses in mice, 11 and in the current study we observed that APOE3 mice also had a reduction in spines in the cortex and hippocampus. It is already established that young adult APOE4 mice have less spines in the cortex, but not hippocampus,[20] and in this study we replicated those results. We had predicted that mTBI would cause more synaptic loss in APOE4 mice, but instead we saw no change in dendritic spines in the dentate gyrus, and an increase in synapses in the cortex after a single mTBI. These data suggest that the activation of subcellular signaling pathways in control of synaptic withdrawal is different in APOE3 and APOE4 mice. One such pathway is the calcium/calmodulin-dependent calcineurin pathway, which when activated causes spine withdrawal.[30] Our data shows that this pathway is activated following mTBI in APOE3 mice, but not in APOE4 mice. The influx of calcium through the NMDA receptor can activate multiple diverse subcellular signaling pathways, and the release of glutamate after TBI is a well-known event that activates NMDA receptors.[31] Multiple factors can influence which subcellular signaling cascade is activated following NMDA receptor stimulation including the frequency, duration and amplitude of calcium input,[32] and the NMDA receptor subunit composition.[33] While there is no data suggesting that APOE has a direct effect on NMDA receptor subunit composition, APOE4 mice do have a lower glutamate pool than APOE3 mice,[34] which may result in less glutamate release following mTBI. Similarly, NMDA-dependent LTP induction in hippocampal APOE4 slices is lower than APOE3 mice suggesting that NMDA function is being modulated by the presence of the apoE4 protein.[29] These changes in NMDA receptor function may be responsible for abnormal sub-cellular signaling cascades after mTBI that result in a stable synapse in the hippocampus, and even increase synaptic growth in the cortex.

Persistent neuroinflammation is a common pathology of single TBI,[35] repeat mTBI in athletes,[36] and CTE,[37] and the APOE4 allele exacerbates chronic inflammation, including in our repeat mTBI model. Previous studies have shown that the APOE4 gene increases inflammation in response to diverse insults including severe TBI[22] and the presence of bacterial envelope proteins.[38] These data suggest that while the APOE4 allele may protect against the acute effect of mTBI, they could worsen the symptoms or pathology of chronic neuroinflammation. This leads to the troubling scenario where APOE4 carriers may be enriching in contact sports as they suffer from fewer acute symptoms of mTBI, but without acute symptoms to signal the presence of a brain injury the athlete may continue to expose themselves to additional head trauma. In the long-term these same athletes are exposing themselves to a higher mTBI yield and are more susceptible to chronic neuroinflammation as a result of those head impacts.

In conclusion, our preclinical data shows that APOE4 carriers require higher force to cause the onset of concussion symptoms, and can recover quickly from concussion. This resilience may explain the enrichment of the APOE4 allele in professional boxers. However, we again stress that while APOE4 may reduce the acute symptoms of concussion, APOE4 carriers can still be concussed, have post-concussion syndrome, and do develop CTE.

Example 2

The inventors have discovered an association of plasma levels of tau with radiological indications of traumatic brain injury (TBI), as measured by MRI, in subjects evaluated for mild head injury. Improved tests are needed to evaluate mild head injuries, which are a common injury. Approximately 2.5 million people in the US seek medical care for head injury each year at an estimated annual cost of $76 billion in direct and indirect costs. Many of these subjects, including those deemed low risk according to accepted clinical guidelines (Canadian Head Rule and New Orleans Criteria), are evaluated using neuroimaging (predominantly head CT scans) despite high costs and associated radiation exposure. Reasons for unnecessary neuroimaging of low risk subjects are controversial. Some have attributed the overreliance on neuroimaging to medicolegal concerns of physicians who prefer an objective test rather than documenting their clinical exam in sufficient detail that it would stand up to scrutiny in the event of a lawsuit. Whereas it is simple to document a medical test, it is time consuming to take an extensive medical history and to document a detailed physical exam. A convenient blood test that correlates with neuroimaging findings could become an important tool for evaluating mild head injury.

Several technical advances made it possible to discovery the correlation of plasma tau levels with MRI indications of TBI. Through a series of technical advances, we have achieved sufficient sensitivity and specificity to measure small changes in levels of plasma in tau. First, we used two capture antibodies that synergistically bind tau with high avidity and specificity. Second, we have optimized the assay to achieve low background when multiplexed. Together, these technical advances make it possible to measure clinically relevant tau levels using plate assays as well as point-of-care cartridges.

Dr. Diaz-Arrastia provided 97 plasma samples from 56 subjects with mild traumatic brain injury. All samples were associated with detailed clinical information, including MRI data.

This correlation between tau levels and MRI findings is significant since tau could be combined with other biomarkers (e.g., plasma levels of GFAP) to improve the sensitivity of blood tests for mild traumatic brain injury. Although plasma levels of tau and GFAP were strongly correlated in our study, tau levels appear to provide additional information not obtained from measurements of GFAP alone. Further testing is needed to determine how best to combine tau with other biomarkers for evaluating and monitoring head injuries.

Example 3

The inventors have discovered that ultrasensitive immunoassays for cytokines and brain-related serum biomarkers were able to detect analytes not only in the serum and plasma of individuals with traumatic brain injury (TBI), Alzheimer's or dementia, but also in the serum and plasma of most apparently healthy individuals. As noted in Example 2, an estimated 2.5 million cases of traumatic brain injury TBI occur in the United States per year. Serum or plasma biomarkers that can indicate the extent of injury may be useful for TBI research. Several analytes whose concentrations are elevated after TBI have been previously described, including inflammatory cytokines and proteins that are mainly expressed in the central nervous system. Serum concentrations for many of these markers are in the pg/mL or even fg/mL range for samples from healthy individuals and thus undetectable by most immunoassay technologies. The inventors have developed an ultrasensitive immunoassay capable of accurately measuring the full concentration range of these markers, allowing levels to be measured in blood samples from healthy individuals and individuals who have suffered TBI. Employing the next-generation S-PLEX assay format, assays for approximately 20 cytokines or TBI markers were developed using MSD's MULTI-ARRAY® electrochemiluminescence technology on MESO® SECTOR S 600 and MESO QuickPlex® SQ 120 instruments. Native and recombinant proteins were used in the development and characterization of the immunoassays. Serum and plasma were tested from healthy controls (n=30), individuals with TBI (n=40), and individuals with dementia or Alzheimer's disease (n=40).

Most S-PLEX cytokine assays had detection limits of approximately 10 fg/ml or better, a dynamic range of typically four orders of magnitude, and were able to detect native analyte in most samples. Median CVs for duplicate measurements were less than 10% for most assays. Concentrations of the following cytokines were elevated for individuals with TBI: IL-1β, IL-2, IL-6, IL-10, IL-22, IP-10, TNFα, and TSLP, along with concentrations of the brain biomarkers NFL, NFH, and GFAP. Due to the sensitivity of S-PLEX technology, NFL, NFH, and GFAP were detectable in all approximately 110 tested samples, including samples from healthy individuals.

Ultrasensitive immunoassays for cytokines and brain-related serum biomarkers were developed. These assays were able to detect analytes not only in the serum and plasma of individuals with TBI, Alzheimer's or dementia, but also in the serum and plasma of most apparently healthy individuals.

Various publications and test methods are cited herein, the disclosures of which are incorporated herein by reference in their entireties for all purposes. In cases where the present specification and a document incorporated by reference and/or referred to herein include conflicting disclosure, and/or inconsistent use of terminology, and/or the incorporated/referenced documents use or define terms differently than they are used or defined in the present specification, the present specification shall control.

REFERENCES

1. Sorbi S, Nacmias B, Piacentini S, et al. ApoE as a prognostic factor for post-traumatic coma. Nat Med. 1995 September; 1(9): 852.
2. Friedman G, Froom P, Sazbon L, et al. Apolipoprotein E-epsilon4 genotype predicts a poor outcome in survivors of traumatic brain injury. Neurology. 1999 Jan. 15; 52(2): 244-8.
3. Mayeux R, Ottman R, Maestre G, et al. Synergistic effects of traumatic head injury and apolipoprotein-epsilon 4 in subjects with Alzheimer's disease. Neurology. 1995; 45(3 Pt 1): 555-7.
4. Mayeux R, Ottman R, Tang M X, et al. Genetic susceptibility and head injury as risk factors for Alzheimer's disease among community-dwelling elderly persons and their first-degree relatives. AnnNeurol. 1993; 33(5): 494-501.
5. Jordan B D, Relkin N R, Ravdin L D, Jacobs A R, Bennett A, Gandy S. Apolipoprotein E epsilon4 associated with chronic traumatic brain injury in boxing. JAMA. 1997 Jul. 9; 278(2): 136-40.
6. Stein T D, Montenigro P H, Alvarez V E, et al. Beta-amyloid deposition in chronic traumatic encephalopathy. Acta Neuropathol. 2015 July; 130(1): 21-34.
7. Bennett R E, Esparza T J, Lewis H A, et al. Human apolipoprotein E4 worsens acute axonal pathology but not amyloid-beta immunoreactivity after traumatic brain injury in 3×TG-AD mice. J Neuropathol Exp Neurol. 2013 May; 72(5): 396-403.
8. Sheng H, Laskowitz D T, Bennett E, et al. Apolipoprotein E isoform-specific differences in outcome from focal ischemia in transgenic mice. JCerebBlood Flow Metab. 1998; 18(4): 361-6.
9. Washington P M, Burns M P. The Effect of the APOE4 Gene on Accumulation of Abeta40 After Brain Injury Cannot Be Reversed by Increasing apoE4 Protein. J Neuropathol Exp Neurol. 2016 Jun. 12.
10. Rhine T, Babcock L, Zhang N, Leach J, Wade S L. Are UCH-L1 and GFAP promising biomarkers for children with mild traumatic brain injury? Brain Inj. 2016 Jul. 14: 1-8.
11. Winston C N, Noel A, Neustadtl A, et al. Dendritic Spine Loss and Chronic White Matter Inflammation in a Mouse Model of Highly Repetitive Head Trauma. Am J Pathol. 2016 March; 186(3):552-67.
12. Miller S A, Dykes D D, Polesky H F. A simple salting out procedure for extracting DNA from human nucleated cells. Nucleic acids research. 1988 Feb. 11; 16(3): 1215.
13. Barber R C, Aragaki C C, Rivera-Chavez F A, Purdue G F, Hunt J L, Horton J W. TLR4 and TNF-alpha polymorphisms are associated with an increased risk for severe sepsis following burn injury. Journal of medical genetics. 2004 November; 41(11): 808-13.
14. Farrer L A, Cupples L A, Haines J L, et al. Effects of age, sex, and ethnicity on the association between apolipoprotein E genotype and Alzheimer disease. A meta-analysis. APOE and Alzheimer Disease Meta Analysis Consortium. JAMA. 1997 Oct. 22-29; 278(16): 1349-56.
15. Hanis C L, Hewett-Emmett D, Douglas T C, Bertin T K, Schull W J. Effects of the apolipoprotein E polymorphism on levels of lipids, lipoproteins, and apolipoproteins among Mexican-Americans in Starr County, Texas. Arterioscler Thromb. 1991 March-April; 11(2): 362-70.
16. Hanis C L, Hewett-Emmett D, Douglas T C, Schull W J. Lipoprotein and apolipoprotein levels among Mexican-Americans in Starr County, Texas. Arterioscler Thromb. 1991 January-February; 11(1): 123-9.
17. Winston C N, Chellappa D, Wilkins T, et al. Controlled cortical impact results in an extensive loss of dendritic spines that is not mediated by injury-induced amyloid-beta accumulation. Journal of neurotrauma. 2013 Dec. 1; 30(23): 1966-72.
18. Kumar A, Stoica B A, Sabirzhanov B, Burns M P, Faden A I, Loane D J. Traumatic brain injury in aged animals increases lesion size and chronically alters microglial/macrophage classical and alternative activation states. Neurobiol Aging. 2013 May; 34(5): 1397-411.
19. Willis F, Graff-Radford N, Pinto M, et al. Apolipoprotein epsilon4 allele frequency in young Africans of Ugandan descent versus African Americans. J Natl Med Assoc. 2003 January; 95(1): 71-6.
20 Dumanis S B, Tesoriero J A, Babus L W, et al. ApoE4 decreases spine density and dendritic complexity in cortical neurons in vivo. J Neurosci. 2099 Dec. 2; 29(48): 15317-22.
21. Banks S J, Miller J B, Rissman R A, Bernick C B. Lack of Influence of Apolipoprotein E Status on Cognition or Brain Structure in Professional Fighters. J Neurotrauma. 2016 Jun. 27.
22. Laskowitz D T, Song P, Wang H, et al. Traumatic brain injury exacerbates neurodegenerative pathology: improvement with an apolipoprotein E-based therapeutic. J Neurotrauma. 2010 November; 27(11):1983-95.
23. Herz J, Beffert U. Apolipoprotein E receptors: linking brain development and Alzheimer's disease. Nat Rev Neurosci. 2000 October; 1(1):51-8.
24. Washington P M, Morffy N, Parsadanian M, Zapple D N, Burns M P. Experimental traumatic brain injury induces rapid aggregation and oligomerization of amyloid-beta in an Alzheimer's disease mouse model. J Neurotrauma. 2014 Jan. 1; 31(1):125-34.
25. Washington P M, Villapol S, Burns M P. Polypathology and dementia after brain trauma: Does brain injury trigger distinct neurodegenerative diseases, or should they be classified together as traumatic encephalopathy? Exp Neurol. 2016 January; 275: 381-8.
26. Hayes R L, Pechura C M, Katayama Y, Povlishock J T, Giebel M L, Becker D P. Activation of pontine cholinergic sites implicated in unconsciousness following cerebral concussion in the cat. Science. 1984 Jan. 20; 223(4633): 301-3.
27. Saija A, Hayes R L, Lyeth B G, Dixon C E, Yamamoto T, Robinson S E. The effect of concussive head injury on central cholinergic neurons. Brain Res. 1988 Jun. 14; 452(1-2): 303-11.
28. Salehi A, Dubelaar E J, Mulder M, Swaab D F. Aggravated decrease in the activity of nucleus basalis neurons in Alzheimer's disease is apolipoprotein E-type dependent. Proc Natl Acad Sci USA. 1998 Sep. 15; 95(19): 11445-9.
29. Dolejsi E, Liraz O, Rudajev V, Zimcik P, Dolezal V, Michaelson D M. Apolipoprotein E4 reduces evoked hippocampal acetylcholine release in adult mice. J Neurochem. 2016 February; 136(3): 503-9.
30. Halpain S, Hipolito A, Saffer L. Regulation of F-actin stability in dendritic spines by glutamate receptors and calcineurin. J Neurosci. 1998 Dec. 1; 18(23): 9835-44.
31 Palmer A M, Marion D W, Botscheller M L, Swedlow P E, Styren S D, DeKosky S T. Traumatic brain injury-induced excitotoxicity assessed in a controlled cortical impact model. J Neurochem. 1993 December; 61(6): 2015-24.
32. Li L, Stefan M I, Le Novere N. Calcium input frequency, duration and amplitude differentially modulate the relative activation of calcineurin and CaMKII. PLOS One. 2012; 7(9): e43810.
33. Santucci D M, Raghavachari S. The effects of NR2 subunit-dependent NMDA receptor kinetics on synaptic transmission and CaMKII activation. PLOS Comput Biol. 2008 October; 4(10): e1000208.
34 Dumanis S B, DiBattista A M, Miessau M, Moussa C E, Rebeck G W. APOE genotype affects the pre-synaptic compartment of glutamatergic nerve terminals. J Neurochem. 2013 January; 124(1):4-14.
35. Johnson V E, Stewart J E, Begbie F D, Trojanowski J Q, Smith D H, Stewart W. Inflammation and white matter degeneration persist for years after a single traumatic brain injury. Brain. 2013 January; 136(Pt 1): 28-42.
36. Coughlin J M, Wang Y, Munro C A, et al. Neuroinflammation and brain atrophy in former NFL players: An in vivo multimodal imaging pilot study. Neurobiol Dis. 2015 February; 74: 58-65.
37. Saing T, Dick M, Nelson P T, Kim R C, Cribbs D H, Head E. Frontal cortex neuropathology in dementia pugilistica. J Neurotrauma. 2012 Apr. 10; 29(6): 1054-70.
38. Zhu Y, Nwabuisi-Heath E, Dumanis S B, et al. APOE genotype alters glial activation and loss of synaptic markers in mice. Glia. 2012 April; 60(4): 559-69.

The invention claimed is:

1. An ultrasensitive assay for detecting Glial Fibrillary Acidic Protein (GFAP) in a sample from a mammal, comprising, in one or more vials, containers, or compartments: (a) a surface comprising (i) a capture reagent for GFAP, said capture reagent bound to the surface, and (ii) an anchoring reagent bound to an anchoring oligonucleotide sequence, said anchoring reagent bound to the surface; and (b) a detection reagent for GFAP that is linked to a nucleic acid probe, wherein the nucleic acid probe comprises an extended sequence that is complementary to the anchoring oligonucleotide sequence bound to the anchoring reagent; wherein the assay is combined to form a proximity-based detection system, and the assay is configured to detect GFAP at a level below 500 femtogram/mL.

2. The assay of claim 1, wherein said assay is configured to detect GFAP at a level below 300 femtogram/mL.

3. The assay of claim 1, wherein said GFAP detection is analyzed on a Meso Scale Discovery (MSD) platform.

4. The assay of claim 1, which is configured to perform a multiplexed assay.

5. The assay of claim 1, which is configured to be conducted in a single assay chamber.

6. The assay of claim 1 comprising, in one or more vials, containers, or compartments: (a) a surface comprising (i) a capture reagent for said biomarkers, said capture reagent bound to the surface, and (ii) an anchoring reagent bound to an anchoring oligonucleotide sequence, said anchoring reagent bound to the surface; (b) a first detection reagent for said biomarkers that is linked to a first nucleic acid probe, wherein the first nucleic acid probe comprises an extended sequence that is complementary to the anchoring oligonucleotide sequence bound to the anchoring reagent; and (c) a second detection reagent for said biomarkers that is linked to a second nucleic acid probe; wherein the assay is combined to form a proximity-based detection system, and the assay is configured to detect said biomarkers at a level below 500 femtogram/ml.

7. The assay of claim 6, wherein said assay is configured to detect GFAP at a level below 300 femtogram/mL.

8. The assay of claim 6, wherein said assay is configured to detect GFAP at a level below 100 femtogram/mL.

9. The assay of claim 6, wherein said assay is configured to detect GFAP at a level below 50 femtogram/mL.

10. The assay of claim 6, wherein said assay is configured to detect GFAP at a level below 25 femtogram/mL.

11. The assay of claim 6, wherein said assay is configured to detect GFAP at a level below 10 femtogram/mL.

12. The assay of claim 6, wherein said assay is configured to detect GFAP at a level below 150 femtogram/mL.

13. The assay of claim 1, wherein said mammal is a primate, non-human primate or a human.

* * * * *